US012630804B2

(12) United States Patent
Alder et al.

(10) Patent No.: US 12,630,804 B2
(45) Date of Patent: May 19, 2026

(54) BLOOD BRAIN BARRIER MODEL

(71) Applicant: UNIVERSITY OF LANCASHIRE, Preston (GB)

(72) Inventors: Jane Alder, Preston (GB); Lisa Shaw, Preston (GB); Claire Lawrence, Preston (GB); Swati Kumar, Preston (GB)

(73) Assignee: UNIVERSITY OF LANCASHIRE, Preston (GB)

( * ) Notice: Subject to any disclaimer, the term of this patent is extended or adjusted under 35 U.S.C. 154(b) by 914 days.

(21) Appl. No.: 16/321,792

(22) PCT Filed: Jul. 31, 2017

(86) PCT No.: PCT/GB2017/052230
§ 371 (c)(1),
(2) Date: Jan. 29, 2019

(87) PCT Pub. No.: WO2018/020274
PCT Pub. Date: Feb. 1, 2018

(65) Prior Publication Data
US 2020/0339956 A1 Oct. 29, 2020

(30) Foreign Application Priority Data

Jul. 29, 2016 (GB) .................................... 1613187

(51) Int. Cl.
| C12M 1/12 | (2006.01) |
| C12N 5/071 | (2010.01) |
| C12N 5/079 | (2010.01) |
| G01N 33/50 | (2006.01) |

(52) U.S. Cl.
CPC ........... *C12N 5/0681* (2013.01); *C12M 25/14* (2013.01); *C12N 5/0622* (2013.01); *C12N 5/0697* (2013.01); *G01N 33/5058* (2013.01); *C12N 2502/086* (2013.01); *C12N 2502/28* (2013.01); *C12N 2503/04* (2013.01); *C12N 2513/00* (2013.01); *C12N 2533/52* (2013.01)

(58) Field of Classification Search
CPC .. C12N 5/0681; C12N 5/0622; C12N 5/0697; C12N 2502/086; C12N 2502/28; C12N 2503/04; C12N 2513/00; C12N 2533/52; C12N 2502/081; C12N 2503/02; C12N 2533/30; C12N 5/0062; C12N 5/069; C12N 5/0691; C12M 25/14; C12M 25/04; C12M 35/08; G01N 33/5058
See application file for complete search history.

(56) References Cited

U.S. PATENT DOCUMENTS

| | | | | |
|---|---|---|---|---|
| 2007/0231887 A1* | 10/2007 | McGrath | ................ | C12M 29/04 |
| | | | | 435/297.5 |
| 2012/0015395 A1* | 1/2012 | Shusta | ................. | C12N 5/0697 |
| | | | | 435/368 |
| 2014/0065660 A1 | 3/2014 | Kim | | |
| 2014/0142370 A1 | 5/2014 | Wong et al. | | |
| 2014/0320378 A1* | 10/2014 | Gracias | .................. | H01Q 1/364 |
| | | | | 343/893 |
| 2015/0079143 A1* | 3/2015 | Lelkes | ................. | C12N 5/0068 |
| | | | | 435/402 |
| 2015/0209284 A1 | 7/2015 | Kuo et al. | | |
| 2015/0240194 A1* | 8/2015 | Neumann | .......... | G01N 33/5085 |
| | | | | 435/348 |
| 2016/0186146 A1 | 6/2016 | Thomson et al. | | |
| 2016/0313306 A1* | 10/2016 | Ingber | .................... | C12M 21/08 |
| 2017/0362584 A1* | 12/2017 | Bani | ...................... | C12N 5/069 |
| 2018/0031465 A1* | 2/2018 | Di Cagno | .......... | G01N 15/0806 |

OTHER PUBLICATIONS

Kim et al. "A 3D human neural cell culture system for modeling Alzheimer's disease."Nat Protoc. Jul. 2015; 10(7): 985-1006. (Year: 2015).*
Baiguera et al. "In vitro astrocyte and cerebral endothelial cell response to electrospun poly(ε-caprolactone) mats of different architecture." Journal of Materials Science: Materials in Medicine vol. 21, pp. 1353-1362 (2010) (Year: 2010).*
Yucel et al. "Tissue Engineered, Guided Nerve Tube Consisting of Aligned Neural Stem Cells and Astrocytes." Biomacromolecules 2010, 11, 12, 3584-3591 (Year: 2010).*
Cucullo et al. "The role of shear stress in Blood-Brain Barrier endothelial physiology."BMC Neurosci. May 11, 2011;12:40. (Year: 2011).*
Cucullo et al. "A dynamic in vitro BBB model for the study of immune cell trafficking into the central nervous system." J Cereb Blood Flow Metab. Feb. 2011; 31(2): 767-777. (Year: 2011).*
Brown et al. "Recreating blood-brain barrier physiology and structure on chip: A novel neurovascular microfluidic bioreactor." Biomicrofluidics. Oct. 26, 2015;9(5):054124. (Year: 2015).*

(Continued)

*Primary Examiner* — Titilayo Moloye
(74) *Attorney, Agent, or Firm* — DUANE MORRIS LLP

(57) ABSTRACT

Provided is a structure composed of a cell population comprising endothelial cells, astrocytes and pericytes, and a 3D (three dimensional) cell growth material within which the cell population is located. The structure has a TEER value of at least 450 $\Omega/cm^2$. The cells of the structure may be derived from the brain. The cells may be human cells, and in particular may be primary derived non-immortalised cells. The structure is particularly suited for use in a model of the blood brain barrier, and the invention also provides such a model. The structure is located in a container, in which it separates a first chamber located on a first side of the structure and a second chamber located on a second side of the structure. The first and second chambers respectively contain first and second liquids in contact with first and second sides of the structure. The liquids mimic the brain extracellular fluid and the blood. The blood brain barrier model provided may be used in models of brain disease, and to investigate uptake of agents into the brain or diseased brain.

12 Claims, 15 Drawing Sheets

(56)         References Cited

OTHER PUBLICATIONS

Cucullo et al. "A new dynamic in vitro modular capillaries-venules modular system: Cerebrovascular physiology in a box." BMC Neuroscience vol. 14, Article No. 18 (2013) (Year: 2013).*

Cucullo et al. "A new dynamic in vitro model for the multidimensional study of astrocyte-endothelial cell interactions at the blood-brain barrier." Brain Res.Oct. 4, 2002;951(2):243-54. (Year: 2002).*

Vandenhaute, et al. "Adapting coculture in vitro models of the blood-brain barrier for use in cancer research: maintaining an appropriate endothelial monolayer for the assessment of transendothelial migration." Laboratory Investigation vol. 96, pp. 588-598 (Feb. 2016) (Year: 2016).*

Deosarkar et al. "A Novel Dynamic Neonatal Blood-Brain Barrier on a Chip." PLoS One. Nov. 10, 2015;10(11):e0142725 (Year: 2015).*

Ugbode et al. "Astrocytes Grown in Alvetex® Three Dimensional Scaffolds Retain a Non-reactive Phenotype." Neurochem Res 41, 1857-1867 (Apr. 2016). (Year: 2016).*

Alvetex "Alvetex FAQ" https://www.reprocell.com/alvetex/alvetex-faq acessed Sep. 13, 2024. (Year: 2024).*

Toyoda et al. "Initial contact of glioblastoma cells with existing normal brain endothelial cells strengthen the barrier function via fibroblast growth factor 2 secretion: a new in vitro blood-brain barrier model"Cell Mol Neurobiol. May 2013;33(4):489-501. (Year: 2013).*

Brown et al., "Recreating blood-brain barrier physiology and structure on chip: A novel neurovascular microfluidic bioreactor" Biomicrofluidics, vol. 9, 054124, 2015, p. 1-15.

Thomsen et al., A Triple Culture Model of the Blood-Brain Barrier using Porcine Brain Endothelial cells, Astrocytes and Pericytes PLoS One, vol. 10, No. 8, Aug. 4, 2015, e0134765.

Al Ahmad et al., "Astrocytes and Pericytes differentially modulate blood-brain barrier characteristics during development and hypoxic insult" J. of Cerebral Blood Flow & Metabolism, 31, Sep. 8, 2010, pp. 693-705.

Urich et al., "Multicellular Self-Assembled Spheroidal Model of the Blood Brain Barrier" Scientific Reports, vol. 3, 1500, Mar. 20, 2013, p. 1-8.

Search Report issued on Apr. 27, 2017 in corresponding application GB1613187.2, 4 pages.

Esposito Carla L et al: "A combined microRNA-based targeted therapeutic approach to eradicate glioblastoma stem-like cells", Journal of Controlled Release, Amsterdam, NL, vol. 238, Jul. 21, 2016 (Jul. 21, 2016), pp. 43-57.

Swati Ashok Kumar: "Developing a physiologically relevant blood brain barrier model for the study of drug disposition in glioma" Thesis, Jul. 29, 2016 (Jul. 29, 2016), XP055406338, Retrieved from the Internet: URL:http://clok.uclan.ac.uk/12873/ [retrieved on Sep. 13, 2017].

International Search Report and Written Opinion in International Patent Application No. PCT/GB2017/052230, dated Sep. 27, 2017, in 15 pages.

Urich, Eduard, et al. "Transcriptional profiling of human brain endothelial cells reveals key properties crucial for predictive in vitro blood-brain barrier models." *PloS one* 7.5 (2012): e38149, 16 pages.

Polikov, Vadim, et al. "In vitro models for neuroelectrodes: A paradigm for studying tissue—materials interactions in the brain." *Indwelling neural implants: strategies for contending with the in vivo environment*, Reichert WM, editor (2008) Boca Raton (FL): CRC Press/Taylor & Francis; 18 pages.

Goodman, Thomas Tyrel, et al.. "3-D tissue culture systems for the evaluation and optimization of nanoparticle-based drug carriers." *Bioconjugate Chemistry* 19.10 (2008): 1951-1959.

Abbott, N. Joan, et al. "Astrocyte—endothelial interactions at the blood-brain barrier." *Nature Reviews Neuroscience* 7.1 (2006): 41-53.

* cited by examiner c

A

B

BLOOD BRAIN BARRIER MODEL

CROSS-REFERENCE TO RELATED APPLICATIONS

This application is a U.S. national phase application filed under 35 U.S.C. § 371 of International Application No. PCT/GB2017/052230, filed on Jul. 31, 2017, which claims the benefit of priority to United Kingdom Patent Application No. 1613187.2, filed on Jul. 29, 2016, the entire disclosures of which are incorporated herein by reference in their entirety for all purposes.

FIELD OF THE INVENTION

The present invention relates to a blood brain barrier model and a structure for use in construction of the blood brain barrier model. The invention also relates to a method of making the blood brain barrier model and a method of investigating the permeability of the blood brain barrier using the model of the invention.

INTRODUCTION

The blood brain barrier is a highly selective physical, transport and metabolic barrier that divides the central nervous system from the blood. A stable microenvironment is essential for neural circuitry, therefore brain homeostasis is highly controlled by the blood brain barrier to avoid disturbances in synaptic and axonal signalling. Neurons are never more than 8-20 μm away from a capillary, therefore the blood brain barrier exerts the greatest control over the immediate microenvironment of brain cells. One function of this control is the ability of the blood brain barrier to prevent movement of molecules across the barrier into the central nervous system.

It is now known that the blood brain barrier includes both a metabolic and a physical barrier in the form of a dynamic interface, whose phenotype is critically dependent on an intact functional neurovascular unit (Abbott et al., 2006). The neurovascular unit is comprised of dynamically integrated endothelial cells, pericytes, astrocytes, neurons and microglia. Tight junctions between endothelial cells prevent paracellular transport and pericytes play a key role in the development of cerebral microvasculature and regulation of blood flow. Astrocytes and the basal lamina support function of neurons, regulate pericyte differentiation and communicate with segments of the microvasculature.

Over the past 30-years there have been various iterations of models designed to mimic the blood brain barrier. These have been created in order to research the characteristics of the blood brain barrier and its behaviour. In particular, given the difficulty many molecules experience crossing the blood brain barrier, there has been an emergence of cell based in vitro models as potential tools to predict the in vivo permeation of molecules such as therapeutics through the blood brain barrier.

Relevant advances in related fields such as nanotechnology, microfluidics and three-dimensional cell growth materials have furthermore been made. The acceptance of the importance of 3D hierarchy, extracellular matrix and the presence of multiple cell types required in culture for effective cell-cell communication has led to developments in the general research area of in vitro modelling (Goodman et al., 2008). In addition, there has been increased emphasis on the importance of species specific models for producing relevant scaling factors for use in in vitro-in vivo correlations (Polikov et al., 2008).

However, having said that, there is currently a lack of an in vitro blood brain barrier model that has been cultured using all human components, and furthermore a lack of a blood brain barrier model that can provide an accurate representation of both the physical and metabolic state of the blood brain barrier in vivo. Currently, the available in vitro blood brain barrier models tend to use non-human cells and have only been characterised for the physical barrier and not the metabolic barrier comprised of the cells of the functional neurovascular unit.

Accordingly, there is a need for a blood brain barrier model which is physiologically relevant and focuses on the metabolic barrier present at the blood and brain junctions with a goal to aiding development of permeable therapeutics for the treatment of brain pathologies.

The present inventors have produced a 3D in vitro model of the blood brain barrier containing cells of the functional neurovascular unit. The model has been has been optimised to express maximal transendothelial resistance, tight-junction, transporter and enzyme expression and activity accurately reflecting both the physical and the metabolic state of the blood brain barrier.

SUMMARY OF THE INVENTION

According to a first aspect of the present invention, there is provided a structure comprising a cell population comprising endothelial cells, astrocytes and pericytes;

and a 3D (three dimensional) cell growth material within which the cell population is located;

wherein the structure has a TEER value of at least 450 $\Omega/cm^2$.

According to a second aspect of the present invention, there is provided a blood brain barrier model comprising a container comprising the structure of the first aspect;

wherein the structure separates a first chamber located on a first side of the structure and a second chamber located on a second side of the structure;

and wherein the first chamber contains a first liquid in contact with the first side of the structure, and the second chamber contains a second liquid in contact with the second side of the structure.

According to a third aspect of the present invention, there is provided a method of making a structure, the method comprising the steps of:

(a) Distributing a cell population comprising endothelial cells, astrocytes and pericytes in a 3D (three dimensional) cell growth material; and (b) Culturing the cell population under shear stress.

According to a fourth aspect of the present invention there is provided a method of investigating the permeability of the blood brain barrier, the method comprising:

(a) Exposing the blood brain barrier model of the second aspect to a test molecule; and (b) Measuring the permeability of the blood brain barrier model.

DESCRIPTION OF THE FIGURES

The invention is further illustrated by the accompanying Figures, in which.

DETAILED DESCRIPTION OF THE INVENTION

Figure 1:
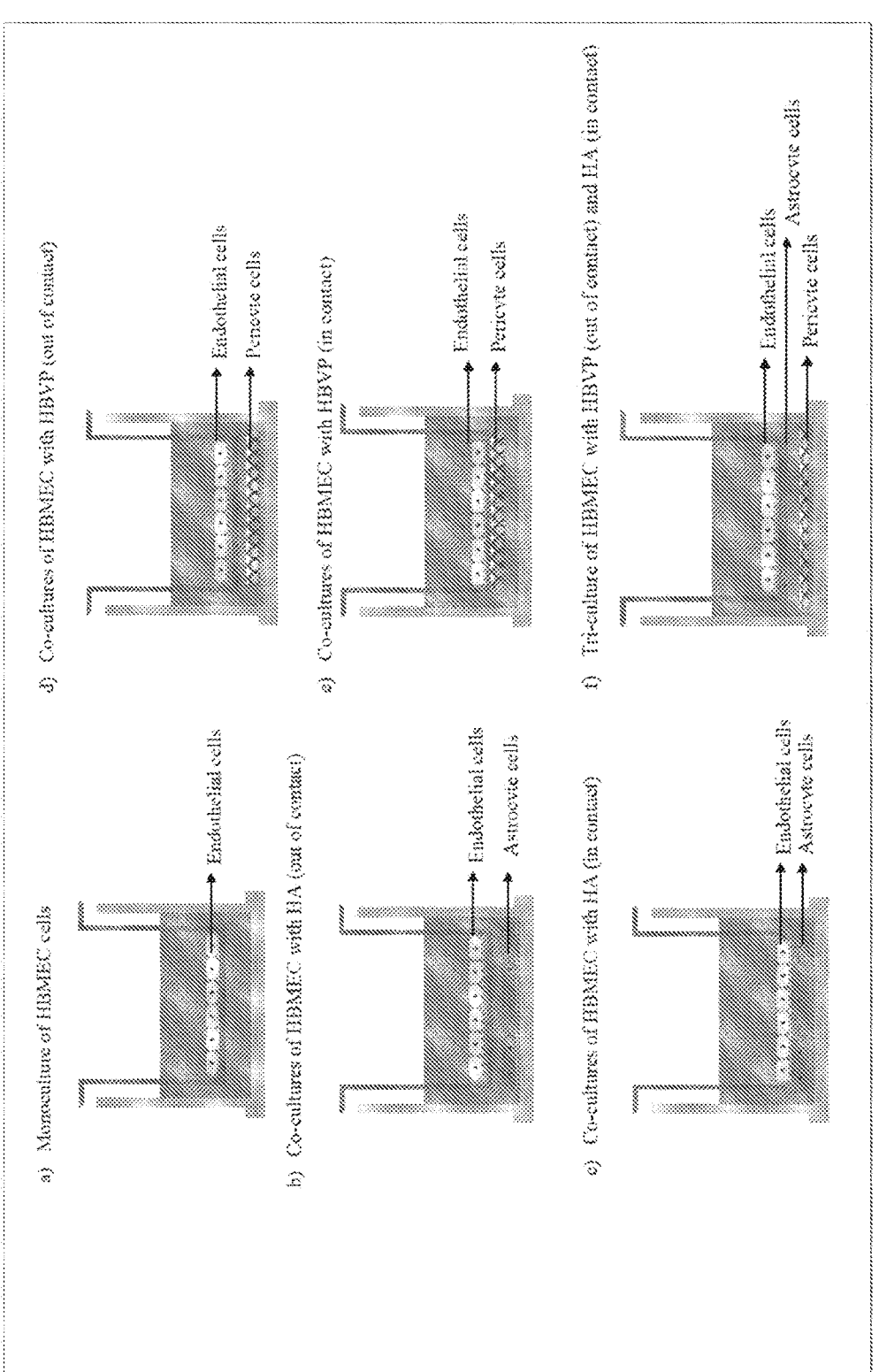
FIG. 1 Illustrates a scheme of the comparative in vitro blood brain barrier transwell models, in which the following cells are present: endothelial monoculture (a); astrocyte and endothelial co-culture out of contact (e/–/a)* (b) and in contact (e/a/–)* (c); endothelial and pericyte co-culture out of contact (e/–/p)* (d) and in contact (e/p/–)* (e) and triculture with pericytes out of contact (e/ap/–)* (f)

The present invention is based upon the inventors' finding that they are able to obtain a more accurate blood brain barrier model by using a cell population appropriate to mimic the functional neurovascular unit having endothelial, pericyte and astrocyte cells located upon and within a 3D cell growth material which supports the cells to maintain their 3D shape, where the cells have been grown under a shear stress The blood brain barrier model of the invention is based on such a structure and provides a much needed in vitro tool for research. In particular it provides a more accurate physical and metabolic reflection of the in vivo blood brain barrier. Without being limited by theory, it is believed that the physical accuracy is provided from growing the cell population under shear stress, this gives the structure of the model a high transendothelial resistance. The metabolic accuracy is believed to be provided from growing the cell population in a 3D manner, this allows the cell population to maintain the arrangement and the tight-junction, transporter and enzyme expression and activity they would do in vivo.

The combination of the more accurate physical and metabolic reflection of the in vivo blood brain barrier model means the present invention is an invaluable tool for researchers.

Prior to the present disclosure, it has not been known to provide a blood brain barrier model that accurately reflects both metabolic and physical states of the in vivo barrier. Specifically, no prior model has used the three cell population of the present invention, within a 3D cell growth material, that has such a high transendothelial resistance. Furthermore, no prior models have used all human, all primary derived non-immortalised cells.

Advantageously, the barrier of the present invention has improved physiological relevance, and therefore is more useful for research into the permeability of the barrier to various molecules, specifically applications in assessing permeability of the barrier to candidate drugs. The barrier of the present invention improves in vitro-in vivo predictions relating to molecules. For example, by providing a more stringent and accurate barrier that will stop over-prediction of CNS bioavailability and will therefore stop unsuitable molecules being selected for development.

The following description of components is intended to apply to each of the aspects of the invention and any embodiments thereof described in the present application in any workable combination.

Structure

As described above, the structure is the key component of the blood brain barrier model because it comprises a cell population of endothelial cells, astrocytes and pericytes located within a 3D (three dimensional) cell growth material intended to reflect the in vivo blood brain barrier structure.

The structure is produced by the method described above, wherein the cell population is distributed in the 3D cell growth material and then the cells are cultured in the 3D cell growth material under shear flow.

The method produces a structure having the property of a relatively high TEER value, and furthermore a structure in which the cells maintain their 3D morphology and in which the cells are free to migrate into their natural 3D organisation as they would in vivo.

This in turn allows a blood brain barrier model to be produced using the structure which mimics the in vivo blood brain barrier. Specifically, the blood brain barrier model mimics the physical property of the high TEER of the blood brain barrier in vivo, and mimics the metabolic property of cells in the blood brain barrier in vivo having high activity of proteins such as transporters and enzymes.

Cell Population

As set out above, the cell population comprises a mixture of endothelial cells, astrocytes and pericytes. Endothelial cells are squamous cells that line the walls of blood vessels. Astrocytes are star shaped glial cells that are located in the central nervous system. Pericytes are contractile cells that wrap around endothelial cells present in blood vessels.

Suitably, the endothelial cells, astrocytes and pericytes are derived from the brain.

Suitably the cells are human cells. The use of human cells provides the advantage of a more accurate reflection of the in vivo blood brain barrier, particularly when investigating the permeability of the blood brain barrier to candidate drugs for example, and avoids inter-species variation.

The endothelial cells may be microvascular endothelial cells. The microvascular endothelial cells may be selected from either human brain microvascular endothelial cells (HBMEC) cells or human cerebral microvascular endothelial cells (hCMEC) cells such as hCMEC/D3 cells. Suitably the endothelial cells are HBMEC cells.

The astrocytes may be human cerebral astrocyte (HCA) cells. Suitably the astrocytes are SC1800 HA cells.

Suitably the pericytes are human brain vascular pericyte (HBVP) cells.

The cells may be non-immortalised cells, or immortalised cells. By non-immortalised cells it is meant cells derived from primary tissue by passaging that have a finite proliferation/division potential and can typically undergo from 2 up to to 60 passage cycles, these cells are referred to herein by the term 'primary derived non-immortalised cells' but may also be known as 'primary derived short term cells'. By immortalised cells it is meant cells that have acquired the ability to proliferate indefinitely, typically by transformation.

Suitably the cells are non-immortalised. The use of primary derived non-immortalised cells provides the advantage of a more accurate reflection of the in vivo blood brain barrier because such cells retain all the natural characteristics of the corresponding cells found in vivo.

Immortalised cells may be produced from primary cells or non-immortalised cells by, for example, the lentiviral vector system (Urich et al. 2012).

Suitably the endothelial cells are either immortalised or non-immortalised cells, and the pericytes and astrocytes are non-immortalised cells.

In one embodiment the endothelial cells are non-immortalised HBMEC cells.

In one embodiment, the endothelial cells are immortalised hCMEC/D3 cells.

In one embodiment, the astrocytes are non-immortalised SC1800 HA cells.

In one embodiment, the pericytes are non-immortalised HBVP cells.

Any suitable source may be used for the cells. For example, cells may be purchased from Lonza Group Ltd. UK, Merck Millipore Ltd. UK, or Sciencell Ltd. UK.

In some embodiments, one or more of the cell types in the cell population may be representative of a disease state. Therefore, suitably one or more of the cell types may be derived from a diseased source, or alternatively may be sourced from a disease model. For example the astrocytes may be an activated astrocyte cell line used in Alzheimer's research.

Alternatively or additionally, the cell population may further comprise a population of diseased cells, for example tumour cells such as glioma cells. Suitably, the diseased cells may be present in the model as spheroids.

In one embodiment, the cell population further comprises glioma spheroids.

The cells may be have been grown through several passages. The cells may have a passage number of less than 30, less than 20, less than 10, less than 5. Suitably the endothelial cells and astrocytes have a passage number of less than 10, suitably between 2-9. Suitably the pericytes have a passage number of less than 6, suitably between 2-5. Low passage numbers have the advantage that the cells have not lost any of their defining characteristics, become quiescent or de-differentiated.

The cell population within the final structure may comprise a total cell count of between about 30,000 to about 3,000,000 cells/cm$^2$ of structure surface area, or between about 60,000 to about 1,500,000 cells, or between about 150,000 to about 900,000 cells, or between about 210,000 to about 600,000 cells, or between about 240,000 to about 450,000 cells, or between about 270,000 to about 3300,000 cells/cm$^2$ of the structure surface area. Suitably the cell population comprises a total cell count of about 300,000/cm$^2$ of the structure surface area.

The cell population within the final structure may comprise equal numbers of endothelial cells, pericytes and astrocytes. Alternatively, the cell population may comprise different numbers of endothelial cells, pericytes and astrocytes. The cell population may comprise a majority of endothelial cells and one of astrocyte or pericyte cells. Suitably the cell population comprises a majority of endothelial cells.

The cell population within the final structure may comprise a ratio of endothelial cells:astrocytes:pericytes of between about 7.5:1:1 to about 1:1:1.

The cell population within the final structure may comprise a ratio of endothelial cells:astrocytes:pericytes of about 7.5:1:1, or about 5:1:1, or about 2:2:1, or about 2:1:2, or about 2:1:1, or about 1:1:1. Suitably, the cell population comprises a ratio of endothelial cells:astrocytes:pericytes of about 2:1:1.

Accordingly, suitably the cell population within the final structure comprises about 150,000 endothelial cells, about 75,000 astrocyte cells, and about 75,000 pericyte cells per $cm^2$ of the surface area of the structure.

Suitably all of the cells used are human cells. Embodiments utilising all human cells may also be used in combination with other human components (such as the 3D cell growth material and/or serum considered below), to provide an "all human" embodiment that is particularly advantageous in its ability to accurately reflect the human in vivo situation in vitro. The physiological relevance of such all human models may be improved by use of primary human cells, although all human models utilising immortalised human cells (whether with primary cells or on their own) still offer significant benefits over the prior art.

Three Dimensional (3D) Cell Growth Material

As set out above, the 3D cell growth material is the component within which the cell population is located to form the structure of the blood brain barrier model.

The 3D cell growth material supports 3D culture of the cell population.

By 3D culture it is meant that the cells of the cell population are able to adopt their natural 3D morphology and distribution within the culture material The 3D cell growth material provides a 3D support within which the cells are held such that the natural 3D morphology of the cells is maintained and such that the natural 3D distribution of cells is supported. The cells can proliferate in three dimensions within the 3D cell growth material and migrate within the 3D cell growth material to form an organisation that mimics the in vivo blood brain barrier and which maintains natural cell to cell interactions.

The 3D cell growth material may be between about 100-300 μm thick, or between about 150-250 μm thick, or between about 175-225 μm thick, or between about 190-210 μm thick. Suitably the 3D cell growth material is 200 μm thick. The use of a 3D cell growth material of this thickness means no cell is more than 100 μm from a source of nutrient media much like the typical in vivo environment.

The 3D cell growth material may be formed from a scaffold or a gel.

In an embodiment where the 3D cell growth material is a gel, the gel may be a hydrogel. The gel may be selected from for example HydroMatrix™ Peptide Hydrogel, MaxGel™ Human ECM, Hystem® Stem Cell Culture, Geltrex®, or Matrigel™.

The gel may comprise a biopolymer. Suitably, the biopolymer is selected from those that are commonly present in the in vivo extracellular matrix, or a combination of those that are commonly present in the in vivo extracellular matrix. For example, Matrigel™ comprises 60% laminin; 30% collagen IV; 8% entactin; heparan sulfate proteoglycan (perlecan); growth factors PDGF, EGF, TGF-β; and matrix metalloproteinases.

In an embodiment where the 3D cell growth material is a scaffold, suitably the scaffold comprises pores.

The pores may be between about 20-100 μm, or between about 25-80 μm, or between about 30-60 μm, or between about 35-50 μm. Suitably the pores are between about 36-40 μm.

The scaffold may comprise a porosity of over 50%, over 60%, over 70%, over 80% or over 90%. Suitably the 3D cell growth material comprises a porosity of over 90%.

The scaffold may be formed from a polymer. The polymer may be selected from those polymers that are suitable for cell culture. Suitably the polymer is inert. The polymer may be selected from, for example, polystyrene, Teflon®, polycarbonate, polyester, or acrylate. Suitably the scaffold is formed from polystyrene.

The scaffold may comprise a foamed material. Suitably the scaffold is a foamed polymer. Suitably the scaffold is foamed polystyrene. One suitable scaffold material is the Alvetex® material produced by Reinnervate, UK.

The scaffold may be coated. The coating may be present upon the scaffold. Suitably the coating covers the surfaces of the scaffold.

The coating may comprise a biopolymer. Suitably, the biopolymer is selected from those that are commonly present in the in vivo extracellular matrix. The biopolymer may therefore be selected from fibronectin, collagen, poly-l-lysine, MaxGel®, or Perlecan. Suitably the scaffold is coated with fibronectin. The extracellular matrix coating provides a physical structure for cell adherence, required for organised tissue structure and it assists in cell-cell communication, allowing a co-ordinated response among groups of cells in response to environmental pressures. The coating also regulates growth of cells and motility of cells.

The coating may be present at between about 1-20 μg/$cm^2$, or between about 2-15 μg/$cm^2$, or between about 3-10 μg/$cm^2$, or between about 4-8 μg/$cm^2$ of surface area of the scaffold. Suitably the 3D cell growth material is coated at 5 μg/$cm^2$ of the surface area of the scaffold.

In one embodiment, the scaffold is coated with 5 μg fibronectin/$cm^2$ of the surface area of the scaffold.

As referred to above, human derived 3D cell growth materials are particularly suitable for use in embodiments in which all of the cells used are human and/or the serum used is human serum. Such all human embodiments are of particularly relevance in reflecting naturally occurring physiological conditions, as set out elsewhere.

TEER Value

Transendothelial electrical resistance (TEER) value is a measurement of the formation of tight junctions between endothelial cells. TEER quantitatively measures the tightness of the blood brain barrier model and acts a surrogate marker of the health of the cells included in the model by measuring their electrical resistance.

The in vivo blood brain barrier is estimated to have a TEER value of 2000 Ω·$cm^2$ as reported from historical literature, therefore in vitro models aim to replicate the same value to imitate the tightness of the blood brain barrier. An increase in TEER observed in a blood brain barrier model indicates a closer representation of the cell organisation and distribution observed in vivo.

The blood brain barrier model of the present invention incorporates a structure having a TEER value of at least about 450 Ω/$cm^2$ as defined above. The TEER value may be at least about 500 Ω/$cm^2$, at least about 600 Ω/$cm^2$, at least about 650 Ω/$cm^2$, at least about 700 Ω/$cm^2$, at least about 750 Ω/$cm^2$. The TEER value may be between about 450 Ω/$cm^2$ and 1000 Ω/$cm^2$, or may be between about 700 Ω/$cm^2$ and 800 Ω/$cm^2$. Suitably the TEER value is about 710 Ω/$cm^2$.

The maximum TEER value of the structure may be about the same as the in vivo TEER value. Suitably the maximum TEER value of the structure is about 2000 Ω/$cm^2$.

By 'about' in the context of TEER it is meant that the TEER value may vary by +/−1-20 Ω/$cm^2$, or by about +/−2-15 Ω/$cm^2$, or by about +/−3-10 Ω/$cm^2$, or by about 4-9 Ω/$cm^2$. Suitably the TEER value may vary by +/−8.2 Ω/$cm^2$.

The TEER value of the structure may be increased by the treating the cells with chemicals that increase the expression of tight junction proteins. For example, the TEER value may be increased by treatment of the cells with retinoic acid.

TEER value may be measured by any known method in the art, such as for example, using the instruments EVOM-2 (Merck Millipore, UK), CellZscope®, or ECIS®.

Suitably the TEER value is measured using the EVOM instrument.

The TEER value of the structure is measured in ohms per centimetre squared. In the event that the TEER value is measured using an instrument with different units of measurement, the readings of that instrument are to be converted into ohms per centimetre squared.

The EVOM instrument, for example, is used to measure the TEER value by a pair of STX2 electrodes of dimensions 4 mm wide and 1 mm thick. Each of the electrodes contains a silver/silver-chloride pellet for measuring voltage and a silver electrode for passing current. The small size of each electrode is designed to facilitate placement of the electrodes into a small scale cellular model. The EVOM not only qualitatively measures cell monolayer health, but also quantitatively measures cellular confluence. The current and voltage flowing between the STX2 electrodes detects the confluence of the cells and correlates with the tightness of the junctions in the blood brain barrier model.

Suitably, the TEER value is a mean value obtained from multiple readings, suitably at least 3 measurements, or at least 4, or at least 5 measurements are taken for calculating a mean.

Suitably, the TEER value is measured across a range of locations in the structure of the blood brain barrier model.

Suitably, the TEER value is obtained by subtracting the TEER value of the 3D cell growth material alone and without the cell population present. The TEER value of the 3D cell growth material alone represents a negative control for the measurement of TEER value.

The Blood Brain Barrier Model

As noted above the blood brain barrier model comprises a container in which the structure is located, and a first and a second chamber separated by the structure located there between. The structure may have a substantially planar form, for example being in the form of a sheet of cells. The first and second chambers each contain liquids in contact with the respective first and second sides of the structure.

The structure divides the container to form the two chambers, one on either side thereof. Therefore the structure comprises a first side and a second side. The first chamber is located on the first side of the structure and the second chamber is located on the second side of the structure. It will be appreciated that a substantially planar structure (which for present purposes may be considered to be one in which ends of the structure are not joined to one another, as may be the case in a tubular or spheroid structure) offers advantages in this context. In particular, the use of a substantially planar structure to divide the container allows a great deal of flexibility in terms of the size of the two chambers formed, and also allows easy access to the contents of both chambers without the need to disrupt constituents of the structure (advantages that are not available in respect of spheroid or tubular structures).

The first and second chambers are intended to mimic the blood side and the brain side of the blood brain barrier.

Suitably, the chamber representing the blood side is known as the apical chamber. Suitably the chamber representing the brain side is known as the basolateral chamber.

Accordingly, one of the first and second sides may mimic the blood side and the other of the first and second sides may mimic the brain side.

The first and second chambers are therefore interchangeable, this is in the context of the requirements of each cell type to contact either the blood side or the brain side of the structure as discussed below.

Accordingly, one of the first and second liquids represents the brain extracellular fluid, and the other of the first and second liquids represents the blood. Suitably, the side comprising a liquid representing the brain extracellular fluid is known as the basolateral side.

Suitably, the side comprising a liquid representing the blood is known as the apical side.

In a similar manner, the first and second liquids are also interchangeable, this is also in the context of the requirements of each cell type to contact either the blood side or the brain side of the structure as discussed below For the purposes of the discussion herein, suitably the first side mimics the blood side and the second side mimics the brain side. Therefore, suitably the first chamber mimics the blood and the second chamber mimics the brain extracellular fluid.

Suitably, therefore, the first side is the apical side and the second side is the basolateral side. Suitably, therefore, the first chamber is the apical chamber and the second chamber is the basolateral chamber.

Suitably therefore, for the purposes of discussion herein, the first liquid is representative of blood and the second liquid is representative of brain extracellular fluid.

In order to preserve the blood brain barrier model as an effective model, the first and second chambers are not in communication and are distinct from one another, so that the first and second liquids are kept separate.

As described above, the structure of the blood brain barrier model comprises a cell population located within a 3D cell growth material.

The cell population is distributed in 3D within the 3D cell growth material.

Therefore the cell population may comprise a particular 3D organisation within the 3D cell growth material.

The cell population may comprise layers within the 3D cell growth material. The structure may therefore comprise a layered cell population.

Suitably there are two or three layers of cells within the 3D cell growth material, the layers being formed from the endothelial cells, astrocytes or pericytes of the cell population. Each layer may comprise one or more of endothelial cells, astrocytes or pericytes of the cell population.

In one embodiment, the first layer of cells is composed of endothelial cells, the second layer of cells is composed of astrocytes, and the third layer of cells is composed of pericytes.

In another embodiment, the first layer of cells is composed of endothelial cells, and the second layer of cells is composed of astrocytes and pericytes.

The structure may comprise a first layer of cells proximal to a first side of the 3D cell growth material, a second layer of cells in the centre of the 3D cell growth material and third layer proximal to the second side of the 3D cell growth material.

Alternatively, the structure may comprise a first layer of cells proximal to the first side of the 3D cell growth material and a second layer of cells proximal to the second side of the 3D cell growth material.

The endothelial cells are located in the layer proximal to the blood side of the structure. This reflects the blood brain barrier structure in vivo.

The astrocytes and/or pericytes are located in the central layer or the layer proximal to the brain side of the structure. This reflects the blood brain barrier structure in vivo.

As noted above, references to the first and second sides of the structure or 3D cell growth material may be interchangeable. However, for the purpose of the present discussion herein, suitably the first side mimics the blood side and the second side mimics the brain side of the blood brain barrier.

Therefore, in one embodiment, the structure comprises a first layer of cells composed of endothelial cells proximal to a first side of the 3D cell growth material, a second layer of cells composed of astrocytes in the centre of the 3D cell growth material, and a third layer of cells composed of pericytes proximal to the second side of the 3D cell growth material.

Therefore, in another embodiment, the structure comprises a first layer of cells composed of endothelial cells proximal to a first side of the 3D cell growth material, and a second layer of cells composed of astrocytes and pericytes proximal to the second side of the 3D cell growth material. This provides the most physiological relevant cell orientation and distribution when referring to the neurovascular unit.

Suitably, as described above, the cell population may further comprise diseased cells. Suitably, the diseased cells may comprise tumour cells, for example glioma cells. Suitably, the diseased cells may form a further layer of the structure. Suitably, the further layer may be positioned anywhere within the structure described above so as to mimic the relevant disease state. Suitably, the layer may comprise droplets of the diseased cells.

Suitably, the diseased cells may be in contact with other cells of the model, or may be out of contact with other cells of the model.

Suitably, in the case of glioma, the glioma cells are positioned in contact with the liquid representing the brain extracellular fluid, suitably on the basolateral side of the structure, suitably on the second side of the structure. Suitably, the glioma cells are positioned beneath the astrocytes.

Suitably, the glioma cells are present as glioma spheroids.

Suitably, the glioma spheroids are comprised in droplets.

Suitably, the glioma spheroids are in contact with the astrocytes.

In either embodiment, the layers may consist of the relevant cell type.

The container of the blood brain barrier model is suitable to house the structure and the first and second chambers.

The structure may be positioned in an insert for insertion into the container.

The insert may be a transwell insert. The container may be a tube, or a well, or a plate, for example. Suitably the container is a well, suitably located on a multiwell plate, for example a 24 well, or a 12 well, or a 6 well plate. A multiwall plate allows for each well to be a separate container and therefore multiple blood brain barrier model experiments can be conducted at once.

The container is suitable to house the insert comprising the structure mounted thereon. Suitably the insert fits within the container.

In one embodiment, the structure is positioned on a transwell insert which is placed and housed in a well of a multiwell plate.

Suitably the structure, when positioned in the insert, forms the base of the insert.

Suitably, the structure mounted upon the insert is disposed approximately in the centre of the container such that the first and second chambers can be on either side thereof.

Optionally, the blood brain barrier model may be miniaturised. Therefore, suitably the container may be a slide, suitably a microscope slide. Suitably, in such an embodiment, the first and second chambers and the first and second liquids are achieved by microfluidic technology Suitably, the container of the blood brain barrier model maybe the same as the culturing vessel described hereinbelow in relation to formation of the blood brain barrier model.

Therefore, the setup may be used in formation of the blood brain barrier model and in the final blood brain barrier model for use.

Optionally, the blood brain barrier model may further comprise fluid flow. The fluid flow may be implemented in the container as described hereinbelow in relation to the culturing vessel. Accordingly, the structure of the blood brain barrier model may be under shear stress.

Formation of the Blood Brain Barrier Model

As described above, the structure of the blood brain barrier model comprises the cell population located within the 3D cell growth material. The structure is located in the container separating the first and second chambers on either side thereof.

To form the blood brain barrier model, first the structure is made using the method described above, then the structure is placed within the container to form the first chamber on a first side thereof and a second chamber on a second side thereof. Then the first chamber is filled with the first liquid and the second chamber is filled with the second liquid, each liquid representing one of the blood or brain extracellular fluid.

The method of making the structure comprises a first step of distributing the cells of the cell population in the 3D cell growth material.

In order for the cell population to be comprised within the structure, the cells are distributed in the structure, in particular, in the 3D cell growth material.

The cells may be distributed in the 3D cell growth material in any known manner.

Distributing the cells may include seeding the 3D cell growth material with the cells or it may include mixing the 3D cell growth material with the cells. Distributing may further include periods of incubation of the 3D cell growth material in order to allow the cells to migrate into the 3D cell growth material, or to allow the 3D cell growth material to set, and in both cases to allow the cells to proliferate The cells may be deposited in numbers lower than that of the cell population in the final structure as defined hereinabove to allow for cell proliferation and growth. Therefore the total cell number distributed in the 3D cell growth material may be around half the total cell population in the final structure.

The cell population distributed in the 3D cell growth material may comprise a total cell count of between about 15,000 to about 1,500,000 cells/cm$^2$ of the surface area of the 3D cell growth material, or between about 30,000 to about 750,000 cells, or between about 75,000 to about 450,000 cells, or between about 105,000 to about 300,000 cells, or between about 150,000 to about 225,000 cells, or between about 135,000 to about 165,000 cells/cm$^2$ of the 3D cell growth material The total cell population distributed in the 3D cell growth material may be around 150,000 cells/cm² of the surface area of the 3D cell growth material.

Optionally, the cell population may be distributed in the 3D cell growth material at lower total numbers than stated above and the culture time may be adjusted accordingly to lengthen the time for the cells to proliferate to the total cell count desired in the structure.

The cells are suitably distributed in their approximate ratios as defined hereinabove in relation to the cell population.

Therefore the numbers of each cell type distributed in the 3D cell growth material may be around 75,000 endothelial cells, 37500 astrocyte cells and 37500 pericyte cells per cm² of 3D cell growth material. This seeding density is optimal to form an intact blood brain barrier model within the 3D cell growth material.

Each of the cell types included in the cell population may be distributed into the 3D cell growth material separately or together in any combination.

Each of the cell types included in the cell population may be distributed into the 3D cell growth material at any location on or within the 3D cell growth material. Suitably, the cell population is distributed on either the first and/or second side of the 3D cell growth material.

The facing sides may be termed the first side of the 3D cell growth material, or second side of the 3D cell growth material as described above.

Suitably as described above in relation to the blood brain barrier model, the cell population is distributed onto the 3D cell growth material so as to form a 3D distribution in the 3D cell growth material, in particular, a layered distribution.

In the first embodiment described above, suitably the endothelial cells are distributed onto the first side of the 3D cell growth material, the astrocytes are distributed into the centre of the 3D cell growth material and the pericytes are distributed onto the second side of the 3D cell growth material.

In the second embodiment described above, suitably the endothelial cells are distributed onto the first side of the 3D cell growth material, and a mixture of astrocytes and pericytes are distributed onto the second side of the 3D cell growth material.

Distributing the cells may comprise seeding the cells.

In either embodiment, the cells on one side of the 3D cell growth material may be distributed first, and the cells in the centre of the 3D cell growth material may be distributed second, and the cells on the opposite side of the 3D cell growth material may be distributed third.

Suitably, the cells for one side of the 3D cell growth material are distributed first, followed by a first period of incubation. Suitably, during the first incubation, the 3D cell growth material is inverted. The incubation allows the cells to attach to the 3D cell growth material.

Suitably, following the first incubation, the 3D cell growth material is inverted, and the cells for the centre and/or opposite side of the 3D cell growth material are distributed, followed by a second period of incubation.

The first period of incubation may be between about 1-8 hours, or between about 2-7 hours, or between about 3-6 hours, or between about 4-5 hours. Suitably the first period of incubation is about 4 hours.

The second period of incubation may be between about 12-36 hours, or between about 15-33 hours, or between about 18-30 hours, or between about 21 to 27 hours, or between about 23-35 hours. Suitably the second period of incubation is about 24 hours Once the cell population has been distributed on the 3D cell growth material and incubated, the cell population is deemed to be distributed within the 3D cell growth material.

Optionally, the method may further comprise a step of distributing a further diseased cell population onto or into the 3D (three dimensional) cell growth material. Suitably, this step may take place at the same time as the above distribution of the cell population or may take place after the cell population has been distributed.

Suitably, the diseased cells are distributed onto the 3D cell growth material. Suitably, after the cell population has been distributed.

Suitably, the diseased cells are distributed onto the 3D cell growth material on the brain side or basolateral side thereof.

Suitably, the diseased cells are distributed onto the 3D cell growth material such that they are in contact with the astrocytes.

Suitably, the diseased cells are distributed onto the 3D cell growth material as droplets.

The method of making the structure comprises a second step of culturing the cells of the cell population under shear stress.

The cells are cultured within the 3D cell growth material under shear stress to form the final structure.

Suitably the cells are cultured by placing the 3D cell growth material comprising the cell population into a culturing vessel.

Therefore, once the cells of the cell population are distributed in the 3D cell growth material, the 3D cell growth material may be positioned on a support. The support may be a transwell support.

The support is suitable to rest within the culturing vessel.

The support may be comprised of a polymer. The polymer is selected from those polymers that are suitable for cell culture; suitably the polymer is inert. The polymer may be selected from, for example, polystyrene, Teflon®, polycarbonate, polyester, or acrylate. Suitably the support is formed from polycarbonate.

The support may be the same as the insert described hereinabove in relation to the blood brain barrier model.

As described below, culturing under shear stress may be achieved by any means.

Suitably the shear stress is exerted in a lateral direction on the cells.

In one embodiment described herein, shear stress is achieved by the use of fluid flow over the structure comprising the cell population.

Therefore, the culturing vessel may further comprise a fluid inlet and a fluid outlet. The inlet is suitably for the ingress of fluid and the outlet is suitably for the egress of fluid. Suitably fluid flow occurs between the inlet and the outlet.

Suitably the structure of the invention is positioned between the fluid inlet and the fluid outlet. Suitably therefore the structure is located in the path of the fluid flow such that suitably a shear stress is exerted by the fluid onto the structure. Suitably, therefore the support comprising the structure thereon is positioned in the path of the fluid flow. Suitably the shear stress is exerted by the fluid onto the support and around the support. Shear stress may therefore be exerted on the cells in the structure in the support by hydrostatic pressure created from the fluid flow around the support.

Suitably the fluid inlet and the fluid outlet are connected to a forced fluid device. The forced fluid device forces fluid through the fluid inlet, into the container and out of the fluid outlet. The forced fluid device may be a pump, more specifically it may be a peristaltic pump. Such pumps are known in the art and may be obtained from, for example, Watson-Marlow Ltd. UK.

The forced fluid device may be connected to the fluid inlet and the fluid outlet by any suitable tubing. The forced fluid device is suitably connected to the fluid inlet by an inlet tube and to the fluid outlet by an outlet tube.

Suitably the forced fluid device is connected to a fluid reservoir, the fluid reservoir containing the fluid.

Suitably the reservoir, forced fluid device, inlet tube, container, and outlet tube from a continuous fluid circuit through which fluid is circulated.

The fluid is suitable for cell growth, suitably therefore fluid is media. The media may be formed from any known culture media or mixture of culture media. Suitably the media comprises a mixture of the culture media for each cell type. Suitably therefore the media comprises a mixture of endothelial cell medium, endothelial basal medium, endothelial growth medium, pericyte cell medium, pericyte growth medium, astrocyte basal medium, and astrocyte growth medium.

The fluid may further comprise additional components for aiding cell growth, such as serum and salt solution. Suitably the serum is human serum. Suitably the salt solution is Hank's balanced salt solution. Serum is added to cultures to promote cell proliferation and maintain in vivo like conditions.

As referred to above, human fluids, such as human serum, are particularly suitable for use in embodiments in which all of the cells used are human and/or the 3D cell growth materials used are human derived. Such all human embodiments are of particularly relevance in reflecting naturally occurring physiological conditions.

The serum may be present in the fluid at a concentration of between about 1% to 10%, or between about 1.5% to 8%, or between about 1.75% to 6%, or between about 2% to 5%. Suitably the serum is present at a concentration of about 2%.

In embodiments where fluid flow is present in the final blood brain barrier model, suitably the fluid is the same as the liquid present in the second chamber of the model.

Media and additional components may be obtained from, for example, Sciencell Ltd. UK.

Suitably the fluid comprises the culture media for each cell type in approximately equal proportions.

Suitably the fluid is changed at appropriate time intervals, such as, for example, every 5 days during culturing of the cells under shear stress.

Suitably the cells are cultured for between 10 to 20 days before use of the structure in the blood brain barrier model, or between 12 to 18 days, or between 13 to 17 days, or between 14 to 16 days. Suitably the cells are cultured for about 15 days before use of the structure in the blood brain barrier model.

The method for producing the structure of the invention may further comprise the step of coating the 3D cell growth material. The coating of the 3D cell growth material is carried out with a coating material. This step may take place before the step of distributing the cell population within the 3D cell growth material as described above.

The coating material is as described above in relation to the 3D cell growth material.

Suitably, coating of the 3D cell growth material comprises covering the surface area of the 3D cell growth material with the coating material. Suitably coating the 3D cell growth material comprises immersing the 3D cell growth material in the coating material. The immersion of the 3D cell growth material may take place for between about 30 minutes to 2 hours, or between about 45 minutes to 1 hour 30 minutes, or between about 50 minutes to 1 hour 10 minutes. Suitably the immersion takes place for about 1 hour.

The method may further comprise a step of washing the 3D cell growth material. The 3D cell growth material may be washed multiple times. Suitably the 3D cell growth material is washed three times. The 3D cell growth material may be washed with any inert liquid. Suitably the 3D cell growth material is washed with PBS. The PBS may be about 0.1M concentration.

Optionally, the 3D cell growth material may be stored in culture medium prior to the step of distributing the cells population therein.

Once the cells have been cultured to form the structure of the invention, the structure may be transferred into the container of the blood brain barrier model as described above.

Alternatively, once the cells have been cultured to form the structure of the invention, the structure may be used in situ within the culturing vessel as the blood brain barrier model. In such an embodiment, the culturing vessel forms the container of the model as described above. In such an embodiment, the culturing vessel may be used with or without fluid flow. The fluid flow and hence the shear stress therefrom may be implemented in the culturing vessel as described above.

Shear Stress

As described above, the cell population is cultured under shear stress within the 3D cell growth material to form the structure of the blood brain barrier model.

The shear stress may be between about 5 to 100 dyne/cm$^2$, or between about 10 to 80 dyne/cm$^2$, or about 15 to 60 dyne/cm$^2$, or about 18 to 50 dyne/cm$^2$, or about 19 to 30 dyne/cm$^2$. Suitably the shear stress is at least 10 dyne/cm$^2$. Suitably the shear stress is less than about 25 dyne/cm$^2$. Suitably the shear stress is about 20 dyne/cm$^2$.

1 dyne/cm$^2$ is equivalent to 0.1 Pa. Accordingly, the shear stress may be between about 0.5 to 10 Pa, or about 1 to 8 Pa, or about 1.5 to 6 Pa, or about 1.8 to 5 Pa, or about 1.9 to 3 Pa. Suitably the shear stress is at least 1 Pa. Suitably the shear stress is less than about 2.5 Pa. Suitably the shear stress is about 2 Pa.

Growth of the cell population under shear stress increases tight junction expression and expression of key transporters and enzymes in the cells which in turn increases the TEER value of the structure. The shear stress allows cells to convert the mechanical stimuli into intracellular signals that affect cellular functions, such as proliferation, apoptosis, migration, permeability, remodelling, and gene expression, which in turn contributes to the cells being able to form a tight and metabolically competent barrier.

Suitably the TEER value is increased by about double when compared to blood brain barrier models that have been constructed without shear stress.

Suitably, expression of tight junction proteins such as occludin and claudin-5 is increased.

Suitably, cell structure and functional remodelling occurs similar to that seen in vivo.

Suitably, the activity of major metabolising enzymes such as cytochrome P450 3A4 and 2D6 increases.

Suitably, the activity of major transporter proteins such as ABCB$_1$ and ABCG$_2$ is increased.

Culturing under shear stress may be achieved by any means.

Suitably, culturing under shear stress may be achieved by fluid flow of over the 3D cell growth material.

Suitably the fluid flow is implemented in the culturing vessel where the structure of the blood brain barrier model is located during formation of the model. Optionally, fluid flow may also be implemented in the container where the structure of the blood brain barrier model is located during use.

Fluid flow may be achieved by the forced fluid device of the blood brain barrier model as described above. The forced fluid device forces fluid to circulate through a fluid circuit defined by a reservoir, forced fluid device, inlet tube, the culturing vessel, and outlet tube.

Suitably the forced fluid circulates under shear flow, the shear flow exerting a pressure within the fluid circuit.

Suitably, as mentioned above, the shear flow is exerted on the structure located in the culturing vessel or container.

Suitably therefore the shear flow is exerted on the cell population located within the 3D cell growth material of the structure.

Once the cell population within the 3D cell growth material has been cultured under shear stress, the final structure of the invention is formed and is ready to use as the blood brain barrier model described above.

Investigating the Permeability of the Blood Brain Barrier

As described above, the invention provides for investigating the permeability of the blood brain barrier in response to various test molecules using the model described herein.

Test molecules may include molecules that increase or decrease, or have no effect on the permeability of the blood brain barrier, or molecules that are intended to pass through the blood brain barrier, or molecules that are intended to be blocked by the blood brain barrier.

Therefore investigating the permeability of the blood brain barrier model may include measuring a change in permeability of the blood brain barrier model in response to or caused by a test molecule, or may include measuring the permeability of the blood brain barrier to a test molecule.

Investigating the permeability of the blood brain barrier may include a test experiment and a control experiment for each molecule being tested. The test experiment may be investigating the permeability of the blood brain barrier model in the presence of a test molecule, or may be investigating the permeability of the blood brain barrier model after exposure to the test molecule. The control experiment may be investigating the permeability of the blood brain barrier model in the absence of a test molecule, or may be investigating the permeability of the blood brain barrier model before exposure to the test molecule.

In one embodiment, the test experiment is after exposure of the blood brain barrier model to the test molecule and the control experiment is before exposure of the blood brain barrier model to the test molecule.

In one embodiment, the test experiment is the blood brain barrier model in the presence of the test molecule and the control experiment is the blood brain barrier model in the absence of the test molecule.

Investigating the permeability of the blood brain barrier may be done when the model is under shear stress or when the model is not under shear stress. Therefore, investigating the permeability of the blood brain barrier may be carried out in the presence or absence of fluid flow.

When measuring a change in permeability of the blood brain barrier model caused by a test molecule, the permeability of the blood brain barrier model may be measured before and after exposure to the test molecule using a molecule of known permeability. This is so that the effect on the permeability of the blood brain barrier of the test molecule can be determined.

Measuring a change in permeability of the blood brain barrier model may comprise:

(a) exposing the blood brain barrier model to a known molecule;

(b) measuring the permeability of the blood brain barrier to the known molecule;

(c) exposing the blood brain barrier model to a test molecule;

(d) exposing the blood brain barrier model to the known molecule for a second time;

(e) measuring the permeability of the blood brain barrier to the known molecule for a second time;

(f) measuring the difference in the permeability of the blood brain barrier to the known molecule between step (b) and step (e); and (g) optionally determining the effect of the test molecule on permeability of the blood brain barrier.

Steps (a) and (b) may optionally be removed from the method if the permeability of the blood brain barrier to the known molecule is already known. The effect of the test molecule in step (g) may be to increase, decrease or have no effect on the permeability of the blood brain barrier.

Measuring the permeability of the blood brain barrier to a test molecule may comprise:

(a) Exposing the blood brain barrier model to a known amount of test molecule; and (b) Determining the permeability of the blood brain barrier model to the test molecule Determining permeability of the blood brain barrier may comprise determining that the blood brain barrier is permeable or impermeable to the test molecule.

Exposing the blood brain barrier model to a molecule, which may be either the test molecule or the known molecule, suitably comprises exposing the structure comprising the cell population to the molecule.

Suitably, exposing the structure to the molecule comprises exposing a first side of the structure to the molecule, the first side being as defined above.

Alternatively, exposing the structure to the molecule may comprise exposing the whole structure to the molecule.

Exposing the structure to the molecule may be achieved by any means. Suitably the exposure of the structure to the molecule is carried out by administering the molecule to the first chamber of the blood brain barrier model, the first chamber being defined above. Alternatively, the exposure of the structure to the molecule is carried out by administering the molecule into the fluid inlet of the fluid flow defined above. Measuring the permeability of the blood brain barrier may comprise measuring the amount of molecule, either a test molecule or a known molecule that has passed through the blood brain barrier model. Alternatively, it may comprise measuring the amount of test molecule in the fluid outlet of the fluid flow. Alternatively, it may comprise measuring the TEER value of the blood brain barrier during exposure to the test molecule. Alternatively, it may comprise measuring extent of efflux of the test molecule by transporter proteins. Alternatively, it may comprise measuring the metabolism of the test molecule by enzymes.

The transporter proteins and enzymes are expressed by and located in the cells of the cell population forming the structure of the blood brain barrier. Suitably, the transporter proteins measured are MDR1 and BCRP transporters. Suitably, the enzymes measured are CYP2D6 and CYP3A4 enzymes.

Suitably, when measuring the efflux and metabolism, the blood brain barrier model is not under shear stress. Suitably, there is no fluid flow present in the blood brain barrier model.

By measuring the TEER value of the blood brain barrier model, researchers can use the model to characterise the effect of a test molecule on the structural characteristics of the model. By measuring the efflux and metabolism of a test molecule, researchers can use the model to characterise the effect of a test molecule on the metabolic characteristics of the model.

Suitably the amount of molecule that has passed through the blood brain barrier model is measured by measuring the amount of molecule to which the blood brain barrier model has been exposed to, and measuring the amount of molecule that has passed through the blood brain barrier model, and determining the difference in the amount of molecule.

Measuring the amount of molecule to which the blood brain barrier model has been exposed to suitably comprises measuring the amount of molecule present on a first side of the structure. Suitably, measuring the amount of molecule present on a first side of the structure comprises measuring the amount of molecule in the first chamber of the blood brain barrier model.

Measuring the amount of molecule that has passed through the blood brain barrier model suitably comprises measuring the amount of molecule present on the opposite side of the structure to the side which is exposed to the molecule. Suitably, the amount of molecule that has passed through the blood brain barrier is measured on a second side of the structure. Suitably, measuring the amount of molecule present on a second side of the structure comprises measuring the amount of molecule in the second chamber of the blood brain barrier model.

The amount of the molecule may be measured by the concentration of the molecule.

The measurement of the amount of molecule may be aided by fluorescent tags conjugated to the molecule, for example the molecule may be FITC-tagged or rhodamine 123 tagged.

The amount of molecule may therefore be measured by the level of fluorescence.

Measurement of the amount of molecule present on a first or second side of the structure of the model may be achieved by imaging both sides of the structure of the model. Various imaging techniques are available in the art, for example when using fluorescent tags, spectrophotometry may be used to image the blood brain barrier model and determine the amount of molecule on either side of the structure.

Measuring the TEER value of the blood brain barrier model may be conducted as described above in relation to TEER value.

Measuring the TEER value of the blood brain barrier during exposure to the test molecule may comprise measuring the TEER value of the blood brain barrier before exposure to the test molecule, and measuring the TEER value during exposure to the test molecule, and determining the difference in the TEER value.

A decrease in TEER value indicates the blood brain barrier is has an increased permeability. This indicates that tight junctions are opening. An increase in TEER value indicates the blood brain barrier has a decreased permeability to the relevant test molecule. If the TEER value stays the same, this indicates that the permeability of the blood brain barrier is unaffected.

The molecule may be selected from candidate drugs or therapeutics, for example: aptamers, short oligonucleotides, pharmaceuticals, nutraceuticals, small molecules, or biologics.

In some embodiments, the invention may comprise investigating the permeability of a diseased blood brain barrier in response to various test molecules.

As described hereinabove, the blood brain barrier may comprise a cell population representative of a disease state. Suitably therefore the blood brain barrier model may comprise diseased cells. Alternatively, mediators of a disease may be introduced into the liquid of the first or second chambers, for example the introduction of inflammatory cytokines into the first liquid. Alternatively, features of a disease may be introduced into the structure of the blood brain barrier model, for example the introduction of glioma spheroids on the brain side of the structure, wherein the glioma spheroids comprise glioma cells.

The blood brain barrier model of the invention may therefore be used to assess the effect of test molecules such as candidate drugs on the relevant in vivo pathology that they are intended to treat. Therefore the method of investigating the permeability of the blood brain barrier may be a method of testing the permeability of the diseased blood brain barrier to candidate drugs.

In one embodiment, the test molecule is an aptamer. Suitably the aptamer may be aptamer GL21. In one embodiment, the test molecule is a small molecule. Suitably the small molecule may be docetaxel or curcumin.

In one embodiment, the test molecule is a miRNA. Suitably the miRNA is miRNA21.

Optionally, the test molecule may be conjugated to a carrier. Suitably the carrier is operable to transport the test molecule and may include nanoparticles, peptides, or the like.

A diseased blood brain barrier model of the invention may be used in comparison with a control 'healthy' blood brain barrier model of the invention to identify novel drug targets. Suitably novel drug targets that are differentially expressed at the blood brain barrier during a disease. For example aptamers that differentially bind to the disease blood brain barrier model but not the control 'healthy' BBB model may be identified and selected. Suitably this may be carried out using SELEX aptamer protocols. An aptamer-assisted precipitation assay may be used to identify the bound aptamer at the blood brain barrier, LC-MS/MS proteomic analysis may be used for identification of the differentially expressed drug target at the blood brain barrier.

Certain embodiments of the invention will now be described by way of reference to the following examples and accompanying figures.

EXAMPLES

1. Methods and Resources
1.1 Cell Lines

The immortalised human cerebral microvascular endothelial cell line (hCMEC/D3), obtained from Merck Millipore (Hertfordshire, UK) is a cell line generated from primary human brain capillary endothelial cells via a lentiviral vector system (Urich et al., 2012). In addition, commercially available short-term cell lines derived from primary tissue including human microvascular endothelial cells (HMBEC), human brain vascular pericytes (HBVP) and human astrocytes (HA) were purchased from (Sciencell, Buckingham, UK). Cells in media and 10% dimethyl sulphoxide (DMSO) were stored in cryovials in liquid nitrogen (−190° C.).

1.2 Media and Supplements

Phosphate buffered saline (PBS), ethanol, all plastic-ware including tissue culture flasks, well plates, centrifuge tubes, stripettes, pasteur pipettes, and 1.5 ml tubes, were purchased from Fisher scientific, Leicestershire, UK. All lab consumables were purchased from Sigma, Dorset, UK unless mentioned otherwise. All the cell lines were cultured in 75 cm2 tissue culture treated flasks and maintained in a 37° C. humidified incubator supplied with 5% CO2 (Thermo Scientific Nunc, UK). Short-term endothelium, pericytes and astrocytes cell lines were grown in endothelial cell media, pericyte media and astrocyte media, respectively (Sciencell, UK). In addition, culture media was supplemented with 5% (v/v) human serum (HS) and growth supplement (Table 1). Frozen cells were rapidly thawed in a water bath at 37° C. and seeded in a 75 cm2 tissue culture flask in a laminar flow cabinet, with 10 mL of growth medium for every 1 ml of defrosted cells. The growth medium was changed after 12-24 h for complete removal of the cryopreservatives. The cells were seeded at a density of 5×104 cells/ml in a 75 cm2 flask which was incubated at 37° C. and 5% CO2 in a humidified incubator until confluent.

TABLE 1

Summary of cell culture supplements

| Reagents | Abbr./storage temperature | Cell line | Suppliers |
|---|---|---|---|
| Endothelial cell medium | ECM, 2-8° C. | HBMEC | Sciencell, UK |
| Endothelial basal media | EBM-2, 2-8° C. | hCMEC/D3 | Lonza, Slough, UK |
| Endothelial Growth Media-2 Single quots | EGM-2, −20° C. | HBMEC, hCMEC/D3 | Lonza, Slough, UK |
| Pericyte cell medium | PCM, 2-8° C. | HBVP | Sciencell, Buckingham, UK |
| Pericyte cell growth supplement | PCGS, −20° C. | HBVP | Sciencell, Buckingham, UK |
| Astrocyte basal media | ABM-2, 2-8° C. | SC1800 (HA) | Lonza, Slough,, UK |
| Astrocyte Growth Media-2 Single quots | AGM-2, −20° C. | SC1800 (HA) | Lonza, Slough,, UK |
| Human serum | HS, −20° C. | HBMEC, hCMEC/D3 HBVP, SC1800 (HA) | Lonza Slough,, UK |
| Hank's balanced salt solution | HBSS, 2-8° C. | All cell lines | Lonza, Slough, UK |

1.3 Comparative Transwell Models

Prior to establishing the three comparative transwell blood brain barrier models, short-term cultures were grown until day 6, to ensure cells were in the exponential phase of growth. The transwell cultures utilised the human microvascular endothelial cells (HMBEC, passage 2-9) human brain vascular pericytes (HBVP, passage 2-5) and human astrocytes (HA, passage 2-9). The three comparative blood brain barrier models are: mono-culture of a single cell type in a transwell plate, co-culture of two cell types in a transwell plate and tri-culture of three cell types in a transwell plate, each of which is cultured under static conditions.

The HBMEC cells were seeded at a density of 50,000 cells/well in mono-culture and 25,000 cells/well in co-culture and tri-culture. In co-culture, the HBVP were seeded at a density of 25000 cells/well and the HA were seeded at a density of 25000 cells/well. In tri-culture, the HBVP were seeded at a density of 12,500 cells/well and the HA were seeded at a density of 12,500 cells/well. The final cell number in each model was always the same and the ratios of the different cell components differed. The ratios of the cells on day one of the TEER measurement was maintained as 1:1:1. The inserts were coated with 5 µg/cm2 of the extracellular matrix (ECM) glycoprotein fibronectin (Sigma, Dorset, UK) for 2 to 4 h and washed with HBSS, pH 7.4.

Co-cultures were defined as 'in-contact' if the insert pore sizes were large enough to allow physical contact between the two cultures (FIGS. 1c and 1e). Cells were first seeded on the basolateral side and incubated in an inverted position for 4 h to enable attachment of the cells, and then transferred to the culture plates and incubated for a further 48 h humidified incubator at 37° C. with 5% $CO_2$. After 48 h, the endothelial cells were seeded in the apical inner chamber of the insert. Co-cultures were defined as 'out of contact' if there was no direct physical contact, for example one cell population on the transwell insert and the other seeded on the bottom of the well in the basolateral chamber. For seeding out of contact co-cultures the cells were seeded on the bottom of the well and incubated in a humidified incubator at 37° C. with 5% $CO_2$ (FIGS. 1b and 1d). After 48 h, the endothelial cells were seeded on the apical side of the insert. All of the co-cultures were cultured in medium of respective cultures utilised, mixed at a ratio of 1:1 (Table 1).

Figure 2:
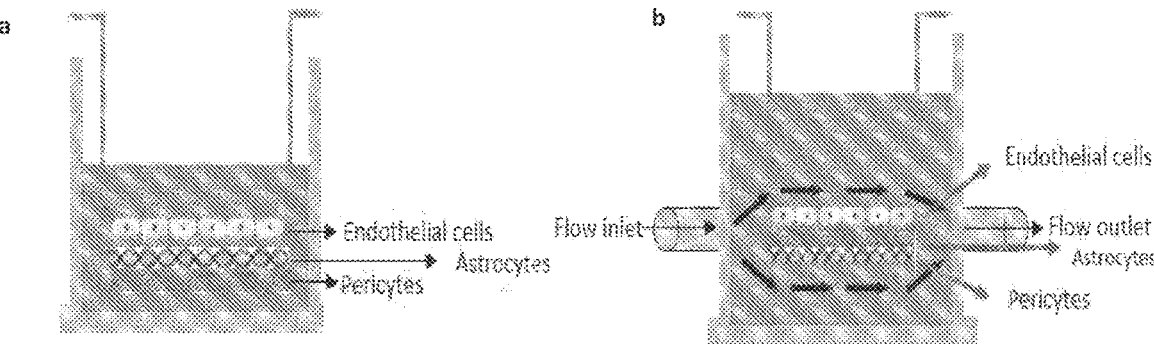
FIG. 2 Illustrates a scheme of (a) the in vitro 3D blood brain barrier model of the present invention and (b) the formation of the in vitro 3D blood brain barrier model of the present invention with shear stress implemented by fluid flow and (c) the in vitro blood brain barrier model of the present invention with inclusion of a cell population representative of a disease state with shear stress implemented by fluid flow.
Figure 2:
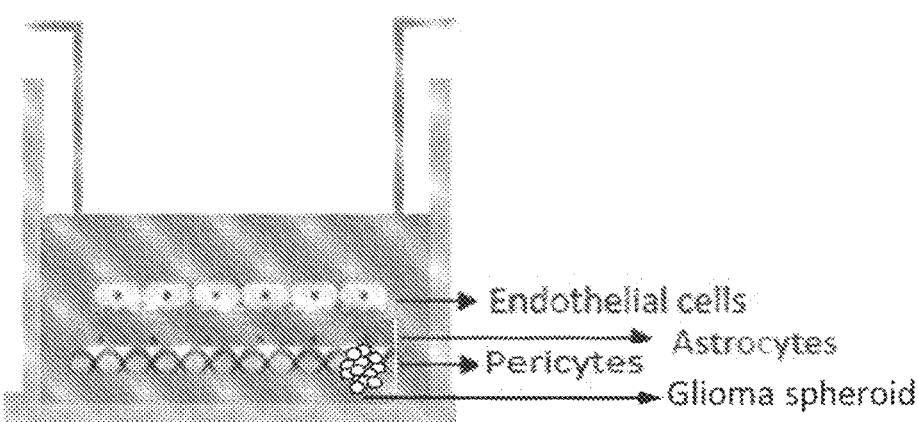

For tri-cultures the astrocytes were seeded on the basolateral side of the insert, with simultaneously seeding of pericytes in the bottom well, or both cell types (astrocytes and pericytes) were seeded on the basolateral side (all-in contact) as seen in FIG. 2a, and both of them were incubated in a humidified incubator at 37° C. with 5% $CO_2$. After 48 h, the insert was placed in the well and the endothelial cells were seeded on the apical side of the insert. The tri-cultures were cultured in medium of respective cultures mixed in a ratio of 1:1:1 (Table 1).

1.4 3D Cell Growth Material Model

The 3D cell growth material model demonstrates the blood brain barrier model of the invention. FIG. 2a illustrates the blood brain barrier model of the invention and FIG. 2b illustrates the formation of the model of the invention under shear stress which comprises of a perfused plate having the Alvetex® 3D scaffold material disposed within it (Reinnervate, Durham, UK) with a peristaltic pump to maintain a shear stress flow of media on the cells growing in the three dimensional (3D) scaffold during culture of the cells. In some instances the model of the invention has been tested either with culture under shear stress or without culture under shear stress. However, the model of the invention is referred to as the '3D model' with shear flow/shear stress or cultured under shear flow/shear stress within the examples, The cells of the 3D model were seeded on the Alvetex® three-dimensional scaffold, precoated in 5 µg/cm2 fibronectin, and then transferred into a perfusion plate. Astrocytes and pericytes were seeded on the basolateral side of the 3D scaffold, and was incubated inverted for 4 h. The 3D scaffold was then placed back in the well and endothelial cells were seeded on the apical side. The plate was incubated for 24 h before the first TEER measurement was taken. The plate was connected to inlet tubing (diameter 16 mm) and outlet tubing (diameter 25 mm) which were connected to a reservoir of media containing mixtures of culture media in equal proportion. Using a peristaltic pump (Watson-Marlow, Cornwall, UK), the pressure of the shear

US 12,630,804 B2

23 stress was set to 20 dyne/cm² and the flow was maintained for a period of 15 days. The medium in the reservoir was changed every 5 days.

FIG. 2c represents an example of how the blood brain barrier model of the invention may comprise a cell population representative of a disease state, for example by the introduction of glioma spheroids. A disease state model was built by incorporating glioma spheroids into the basolateral (brain side) of the structure to create in effect a blood-tumour barrier model. The glioma cells were produced as follows: tissue culture plates were coated with 1% sterile agar and left to cool one day prior to seeding cells for spheroids. Passaged U87MG glioma cells were seeded onto agar coated 24-well plates at a density of 3,000 cells/well. The plates were incubated at 37° C. and 5% CO₂ in a humidified incubator for 6 days, the media was changed after 3 days. On the sixth day, 25 µL media droplets containing the spheroids were directly placed in contact with the astrocytes on the basolateral side of the blood brain barrier model (generally produced as described above). The drops were arranged to hang upside down or out-of-contact in the bottom of the basolateral chamber. Other disease state models were also made with the glioma spheroids placed in contact with the astrocytes (not shown).

1.4 Transendothelial Electrical Resistance Measurements

After 24 h the mono, co-, tri- and 3D scaffold cultures were measured for their transendothelial electrical resistance (TEER) using the EVOM-2 (Merck Millipore, Oxford, UK) across five locations on the insert for each of the models every day for 15 days. Each model was set-up in triplicate to assess intra-assay variability and every experiment was repeated three times to assess inter-assay variability. The TEER value of blank transwell insert was 35 Ω/cm2 and 3D scaffold was 42 Ω/cm2. These blank readings were subtracted from the final measurement to give the TEER value of the set up model. An increase in TEER, detected with the electronic circuit of the meter and its electrode, is an indication of cell monolayer health and confluence.

1.5 Fluorescent Immunostaining

The cells were seeded at a density of 1×104/ml on 1 mm thick coverslips in a 24 well plate and fixed by incubation with 4% paraformaldehyde (PFA) for 15 min at room temperature followed by washing with 0.1 M PBS. Cells were incubated with 0.1 M glycine for 10 min for quenching background fluorescence, washed with 0.1 M PBS, pH 7.4 five times, then permeabilised by incubating with 0.1% triton X-100 for 10 min at room temperature, followed by washing with 0.1 M PBS, pH 7.4 five times. Cells were blocked by incubating with 10% goat serum for 1 h, followed by three washes with 0.1 M PBS, pH 7.4. Cells were then incubated with respective dilutions of rabbit polyclonal primary antibody (Table 2) for 1 h at room temperature and at the end of the incubation period were washed with 0.1 M PBS, pH 7.4 three times. The cells were then incubated with 1:1000 dilution of secondary antibody Alexa Fluor® 488 F(ab')2 Fragment of Goat Anti-Rabbit IgG (Life technologies, UK) for 30 min in the dark. The cells were washed and mounted on a microscope slide using with VECTASTAIN mounting media (Vector Laboratories, Peterborough, UK) and incubated for 24 h in dark, before analysis.

24

TABLE 2

List of primary antibodies, source and dilutions used for immunostaining.

| Primary antibody | Antibody dilutions in 0.1M PBS, pH 7.4 | Manufacturer |
|---|---|---|
| GFAP | 1:300 | Abcam, Cambridge, UK |
| HLA | 1:250 | Santacruz, Middlesex, UK |
| MDR | 1:250 | Abcam, Cambridge, UK |
| BCRP | 1:200 | Abcam, Cambridge, UK |
| Occludin | 1:250 | Abcam, Cambridge, UK |
| Claudin-5 | 1:250 | Abcam, Cambridge, UK |
| Isotype Control | 1:100 | Santacruz, Middlesex, UK |

1.6 Protein Extraction and Quantification

Cells were cultured in T-75 flasks until 70-80% confluence, washed with ice cold 0.1 M PBS, pH 7.4, scraped from the flask using a sterile cell scraper and collected in a precooled 1.5 ml tube to which 500 µl of ice cold RIPA lysis buffer was added. Cells grown on inserts were washed twice with HBSS, pH 7.2 and then incubated with 100 µl RIPA buffer for 15 min at 4° C. The samples were agitated at 40 rpm on a shaker (VXR Vibrax, Oxfordshire, UK) for 30 min at 4° C. to facilitate membrane lysis. The samples were then spun in a microcentrifuge (Sanyo, Leicester, UK) at 11451×g for 20 min at 4° C. After centrifugation the supernatant, was collected in a precooled 1.5 ml tube, ready for determination of protein concentration. The Bradford assay was used for protein quantification where a set of bovine serum albumin (BSA) protein standards diluted in RIPA lysis buffer (0.1 to 2 mg/mL) were used as a reference. Samples and standards were diluted in Bradford reagent (1 in 51 dilutions) in a 96-well plate. The absorbance was read at 612 nm using a plate reader Tecan GENios Pro® (Tecan, Theale, UK). The absorbance of BSA samples were plotted against concentration of BSA and a line of best fit was determined by linear regression, to allow determination of the extracted protein concentration. Protein concentrations were then corrected for dilution factors.

1.7 Western Blotting

Western immunoblotting was used for detection of cytochrome P450 enzymes; CYP3A4, CYP2D6, the efflux transporters; ABCB1 and ABCG2 and tight junction proteins; occludin and claudin-5 protein expression in the extracted protein lysate. The 2 mg/ml protein aliquots from cells, stored at −20° C., were thawed and mixed with 2×Laemmli sample loading buffer at a ratio 1:1 and heated (Techne, Staffordshire, UK) for 5 min at 90° C. Electrophoretic separation was conducted using SDS PAGE using a 4% stacking gel and 10% resolving gel at a constant voltage of 120 V for 2 h. The gel was transferred onto a nitrocellulose membrane by the wet method for 1 h at 90 V in an ice bath. Protein transfer was visualised by Ponceau S red stain then blots were washed and blocked (1 M tris buffer saline with 0.1% tween 20 and 5% non-fat milk), for 1 h at room temperature prior to incubation with the relevant rabbit polyclonal primary antibody (Table 3), overnight at 4° C. The secondary antibody conjugated to horseradish peroxidase (1:10000 dilution) (Table 3) was incubated with the blot for 1 h at room temperature, before washing three times with TBST. The blot was then rinsed with dH2O and the proteins were detected using an ECL plus kit (GE Healthcare, UK) as per the manufacturer's instructions and imaged in a gel doc XPS (Bio Rad, Deeside, UK) to visualise bands of proteins of interest by chemiluminescence.

TABLE 3

List of primary antibodies and dilutions

| Antibody | Antibody dilution (Antibody diluted in 0.1M TBST, pH 7.4) |
|---|---|
| CYP 3A4 | 1:3500 |
| CYP 1B1 | 1:3000 |
| CYP 2E1 | 1:3000 |
| CYP 2D6 | 1:3000 |
| BCRP (ABCG2) | 1:2000 |
| MDR-1 (ABCB1) | 1:3000 |
| β actin (loading control) | 1:5000 |
| Occludin | 1:2000 |
| Claudin-5 | 1:1000 |
| Secondary Antibody (donkey polyclonal secondary antibody to rabbit IgG/mouse IgG) | 1:10000 |

1.8 Activity Assay for Drug Metabolising Enzymes (CYP3A4 and CYP2D6)

The functional activity of CYP3A4 and CYP2D6 in cell lines was assayed in 96-well plates by incubation with a substrate probe for the CYP of interest and measurement of the rate of formation of fluorescent metabolite. The probe used for the CYP3A4 enzyme was 7-benzyloxy-4-trifluoromethyl-coumarin (BFC) (BD Gentest©, Oxford, UK), which formed the fluorescent metabolite 7-hydroxy-4-trifluoromethylcoumarin (HFC) (BD Gentest©, Oxford, UK). The activity of CYP2D6 was determined using 3-[2-(N, N-diethyl-N-methylammonium) ethyl]-7-methoxy-4-methylcoumarin (AMMO) (BD Gentest©, Oxford, UK), which formed the fluorescent metabolite 3-[2-(N,N-diethyl-N-methylammonium) ethyl]-7-hydroxy-4-methylcoumarin (AHMC) (BD Gentest©, Oxford, UK). All substrates and metabolite were dissolved in DMSO to give a 10 mM stock and diluted 1 in 400 in media prior to use to ensure final solvent concentration in the reaction well did not exceed the threshold of 0.1%. The co-factor 10 mM NADPH (stored −80° C.) was freshly prepared in 0.1 M PBS buffer (pH 7.4) and added to the flat bottom, transparent 96-well plate containing pre-warmed (37° C.) 5000 cells/well, substrate at a final concentration of 25 µM and 0.1 M potassium phosphate buffer, pH 7.4 to initiate the enzyme reaction. The formation of HFC was measured at excitation wavelength of 410 nm and emission wavelength of 510 nm and the formation of AHMC was measured at excitation wavelength of 390 nm and emission wavelength of 460 nm in a Tecan GENios Pro® plate reader (Tecan, Theale, UK). Measurements were made at 37° C. every 30 s for 30 min with orbital shaking for 5 sec before each reading. The plates were read from the top, and gain was optimised on the first run and was set at 35 for all subsequent runs. Positive controls, were overexpressed human recombinant CYP3A4 and CYP2D6 in bactosomes (Cypex, UK) were and negative controls included a vehicle control, cells, media or buffer and 0.1% DMSO, substrate blank (cells and media) and enzyme blank (substrate and media). A standard curve of the metabolites was prepared using standard concentrations of HFC or AHMC between 0 to 40 µM, added to 0.1 mg/mL cellular protein to a final well volume of 250 µL in a 96-well plate. The fluorescence emission readings from the kinetic experiment were converted µM HFC or AHMC produced per min, normalised to 1 mg/ml of protein. The Michaelis-Menten plot of rate of enzyme activity verses substrate concentration was plotted using GraphPad Prism™ 6.05, and the Vmax and Km were estimated.

1.9 Activity Assay for Efflux Transporter (ABCB1 and ABCG2)

The multidrug resistance direct dye efflux activity kit (Merck Millipore, Oxford, UK) was used to measure the functional activity of ABCB1 and ABCG2 by assaying the ability of the cell to extrude fluorescent ABCB1 and ABCG2 substrate dyes, 3,3'-Diethyloxacarbocyanine Iodide [DiOC2 (3)] solution and rhodamine 123 solution respectively. A non-fluorescent substrate vinblastine was used as a competitive inhibitor of ABCB1 and ABCG2 transporter activity and DMSO was included as a vehicle control. Cells were extracted from the insert by scraping from the cell culture dishes and trypsinised from the transwell mono-, co-, tri- or 3D cell growth material model. The transporter, activity measurements were carried out on the cell suspension of approximately $2.5 \times 105$ cells according to the kit instructions.

1.10 Permeability of FTIC Dextran

Permeability was assessed using Evan's Blue (10 µg/ml) as a negative control and 100 µg/ml FITC-dextran (mol wt 70 kDa) prepared in media. The media from the apical side of the insert was removed and media containing FITC-dextran was introduced in the culture set up. The fluorescent tagged dextran was incubated on apical side and the media was sampled on the basolateral side to measure the apparent permeability (Papp) of the model. The models were incubated in standard tissue culture conditions and at different time intervals (15 min, 30 min, 45 min, 60 min and 120 min) the media from the basolateral side of the insert was sampled. The fluorescence of the sampled media was read at excitation wavelength 492 nm and emission wavelength 518 nm on a Tecan GENios Pro® plate reader with the gain set at 55 (Tecan, Theale, UK), and converted to concentration using a standard curve of fluorescence verses known concentrations of FITC-dextran.

The apparent permeability of each aptamer was calculated using the formula in Equation 1 (Artusson, 1990). All data was obtained from three experimental replicates.

$$P_{app} = \frac{V}{A \times C_0} \times \frac{dQ}{dt} \qquad \text{(Equation 1)}$$

Where:
V=Volume of basolateral compartment (0.5 cm3)
A=surface area of the polycarbonate membrane (0.3 cm2)
$C_0$=Final concentration of the FITC-dextran in the apical side (100 µg/ml)
dQ=Concentration of FITC-aptamer passing across the cell layer to basolateral side (µg/ml)
dt=Time (min)

1.11 Applications of the Invention

The blood brain barrier model was exposed to a test/known compounds to determine permeability. The final concentration of compound introduced to the apical well was determined previously using a viability assay, and a concentration chosen that minimised toxicity to the BBB cells ($<IC_{50}$). Test compounds (short DNA oligonucleotide glioma selective aptamers (100 nM) tagged with cy5 (GL21, scrambled) and lipid nanoparticles (NPs) loaded with 0.33 µg/ml docetaxel or 2.87 µg/ml curcumin tagged with rhodamine123 and transferrin ligand) were prepared in house. When the TEER values for the BBB model peaked, 3.33 µg/ml Evans Blue Dye (EBD) was added to the apical side of the BBB model to determine if the barrier formed was intact. The test and control compounds were introduced to the well and time dependent TEER measurements were taken along with fluorescent measurements of samples at time points between 0.5-6 h from the basolateral side of the well for determination of appearance of the fluorescent tagged compounds. The NPs were also incubated in BBB models with and without inhibitor for efflux transporters (2 μM vinblastine). The activity was calculated as % fluorescence relative to the stock concentration of the NPs and then plotted An example of how mediators of a disease may be investigated in the blood brain barrier model was via transfection of cells with anti-sense oligonucleotides to quench the effects of elevated microRNA-21 associated with glioma cell invasion, apoptosis, and proliferation. The cells were transfected with hsa-miR-21-3p inhibitor plasmid using jetPRIME® transfection reagent. Briefly, the hsa-miR-21-3p inhibitor was reconstituted in Tris EDTA (TE) buffer and added to the cells in a concentration of 100 nmol/L. The cells were also incubated with 6 μl of jetPRIME® reagent and 200 μl of jetPRIME® buffer. The transfection medium was replaced by growth medium after 6 h. After 48 h, cells the blood brain barrier model was constructed and remaining cells were trypsinised and used to study the expression and activity of ABCB1 and ABCG2 transporters. The results of this study are described in more detail below, and are shown in the Figures.

1.12 Statistical Analyses

All data were expressed as mean values±standard deviation (mean±SD) with n=3 of triplicate experiments. Statistical analysis was carried out using GraphPad Prism (v6.04). Data was checked for normality prior to using the one way ANOVA with Bonferroni post-hoc analyses. Probability values of $p<0.05$ were considered statistically significant.

Figure 3:
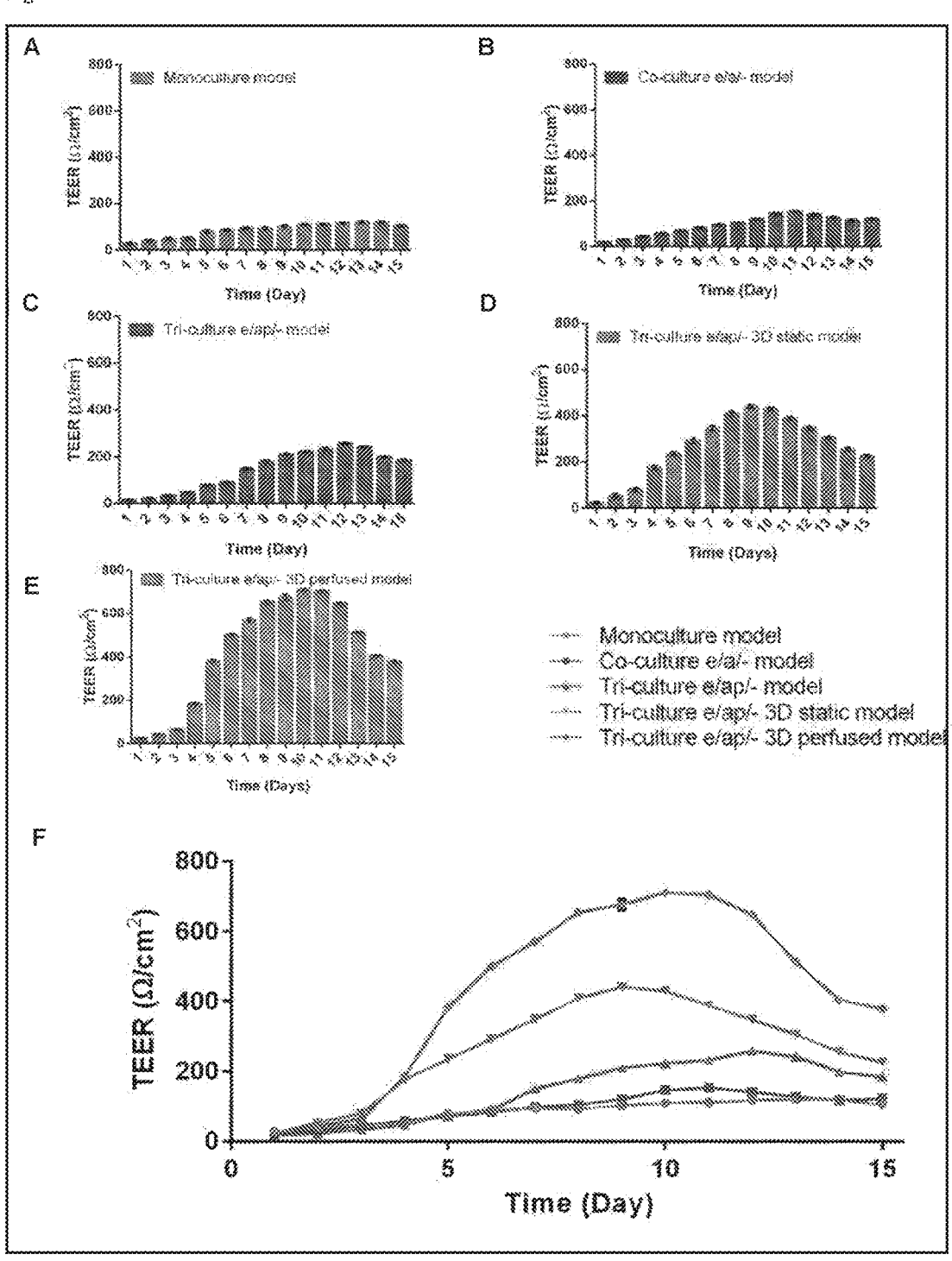
FIG. 3 illustrates the mean±SD TEER measurements (n=5) verses time for mono-culture (A), co-culture (B), tri-culture (C), 3D-static (D) and 3D-shear stress cultures (E) and combined for comparison (F)

2. Results 2.1 Comparison of Three Transwell Models and 3D Cell Growth Material Model of the Invention with Respect to TEER The transwell insert tri-culture was compared to the three-dimensional cell growth material culture (using Alvetex® in the present examples) cultured with and without shear stress, under the same optimised experiments conditions (human serum concentration, cell number and orientation of cell seeding, extracellular matrix and composition) (Table 9). In conclusion, use of a three-dimensional scaffold (FIG. 3d) resulted in a significant increase in TEER from 258±5.31 Ω/cm$^2$ to 440±7.9 Ω/cm$^2$ compared to the tri-culture model on a transwell insert (FIG. 3c). Furthermore, the TEER increased further to 710±8.2 Ω/cm$^2$ when the 3D Alvetex® model was cultured under shear stress flow (FIG. 3d).

The change from culture on a 2D insert to a 3D scaffold was more representative of the 3D tissue organisation observed in vivo; which was reflected in the increase in TEER values. As shown here the induction of shear stress improved the expression of tight junction proteins and increased the TEER values in the in vitro blood brain barrier model.

TABLE 9

TEER values of the different models.

| | Maximum TEER ± SD (Ω/cm$^2$) |
| --- | --- |
| Static tri-culture model | 258 ± 5.31 |
| Static 3D model | 440 ± 7.9 |
| Shear stress 3D model | 710 ± 8.2 |

2.2 Expression of Tight Junction Proteins

Figure 4:
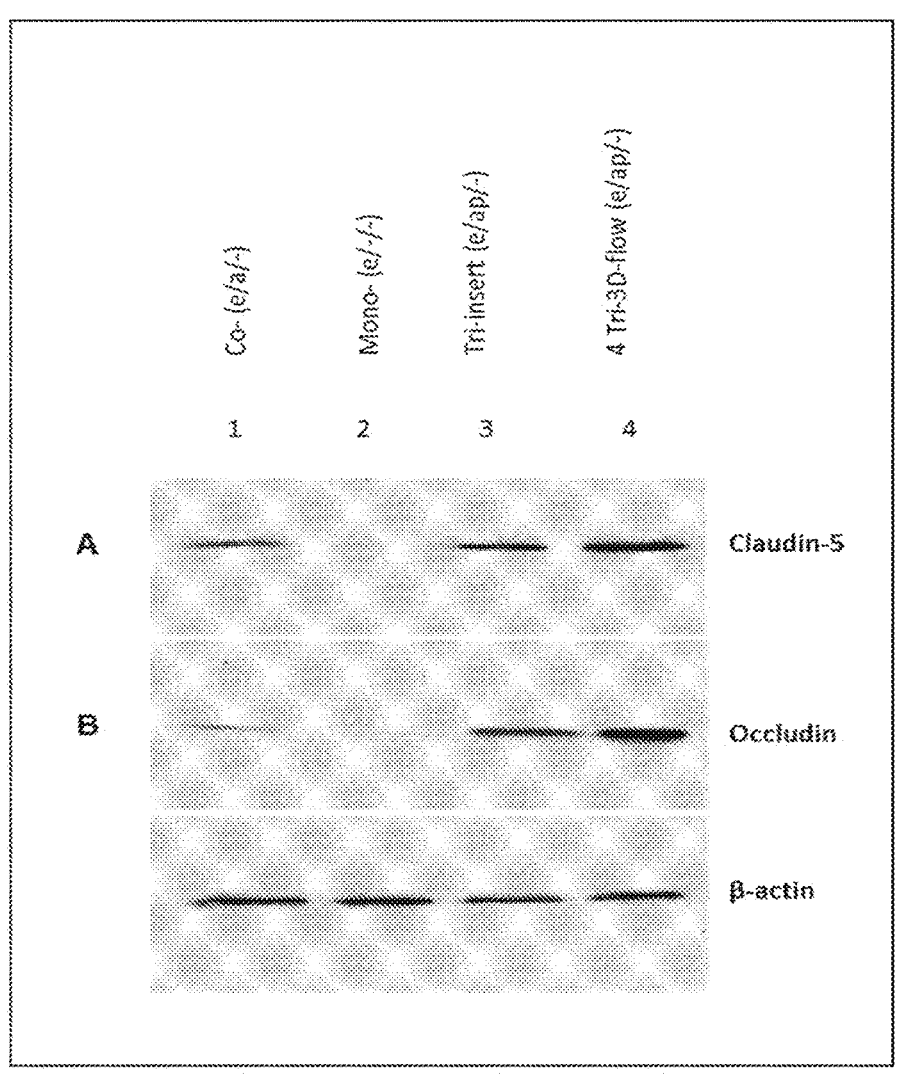
FIG. 4 illustrates western blots of tight junction protein expression: A. Western blot of different models for occludin protein (65 kDa). B. Western blot of different models for claudin-5 protein (23 kDa). Each well was loaded with 10 μg protein. β-actin protein (42 kDa) was used as the loading control.
Figure 5:
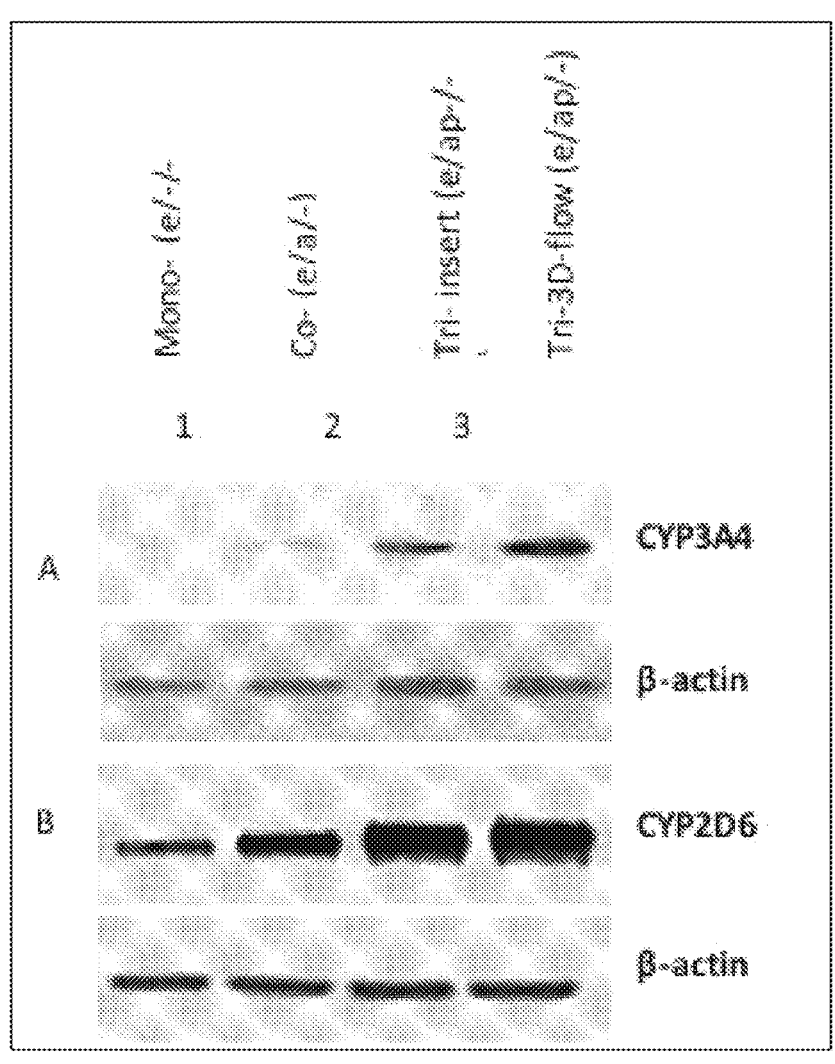
FIG. 5 illustrates western blots of CYP450 enzyme expression: A. Western blot of different models for CYP3A4 (57 kDa). B. Western blot of different models for CYP2D6 (55 kDa). Each well was loaded with 10 μg protein. β-actin protein (42 kDa) was used as the loading control.

The same models were studied for the expression of the tight junction proteins, occludin and claudin-5 (FIGS. 4A & B). The Tri-culture insert model e/ap/– (Lane 3) and the 3D model cultured with shear flow e/ap/– (Lane 4) showed a higher expression of tight junction proteins occludin and claudin-5 when compared to the mono-culture (Lane 2) and co-culture (Lane 1) models. The data showed highest expression of claudin and occludin for the 3D model cultured with flow. Therefore, it is derivable that exposure of endothelial cells to shear stress flow causes an increases the RNA levels of genes encoding for a variety of tight junctional proteins, and increases protein expression thereof 2.3 Drug Metabolising Enzyme and Transporter Expression and Activity In Table 10 is shown enzyme activity data for the two major human drug metabolising enzymes cytochrome P450 (CYP)3A4 and CYP2D6, in each of the blood brain barrier models investigated. The highest enzyme activity was observed in the 3D model cultured with flow. Protein expression with co- and tri-culture models was also measured by Western immunoblotting (FIG. 5).

TABLE 10

Rate of cytochrome P450 enzyme activity in BBB models

| Models | CYP3A4 Rate at 25 μM [S] (μM HFC/min/mg protein) | CYP2D6 Rate at 25 μM [S] (μM HFC/min/mg protein) |
| --- | --- | --- |
| e/—/— | 0.365 | 0.359 |
| e/—/p | 0.389 | 0.377 |
| e/p/— | 0.419 | 0.416 |
| e/—/a | 0.434 | 0.421 |
| e/a/— | 0.459 | 0.437 |
| e/ap/— | 0.483 | 0.479 |
| e/ap/— 3D model cultured with shear flow | 0.621 | 0.598 |

Figure 6:
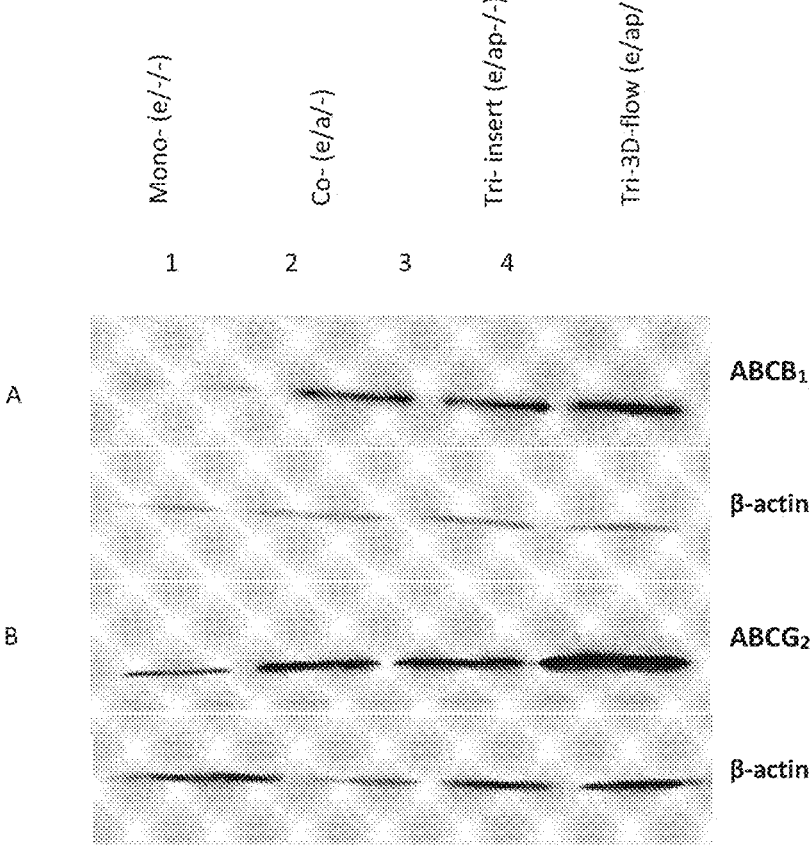
FIG. 6 illustrates western blots of efflux transporter proteins expression: A. Western blot of different models for ABCB1 transporter (170 kDa). B. Western blot of different models for ABCG2 (72 kDa). Each well was loaded with 10 μg protein. β-actin protein (42 kDa) was used as the loading control.

The same models were studied for the expression of ABCB1 and ABCG2 efflux transporter proteins by Western immunoblotting (FIGS. 6A & B). The Tri-culture on insert model (Lane 3) and 3D model cultured with shear flow (Lane 4) showed a higher expression of expression of ABCB1 and ABCG2 efflux transporter when compared to mono-culture (Lane 1) and co-culture (Lane 2) models. The data showed highest expression of ABCB1 and ABCG2 efflux transporter for the 3D model cultured with flow.

Figure 7:
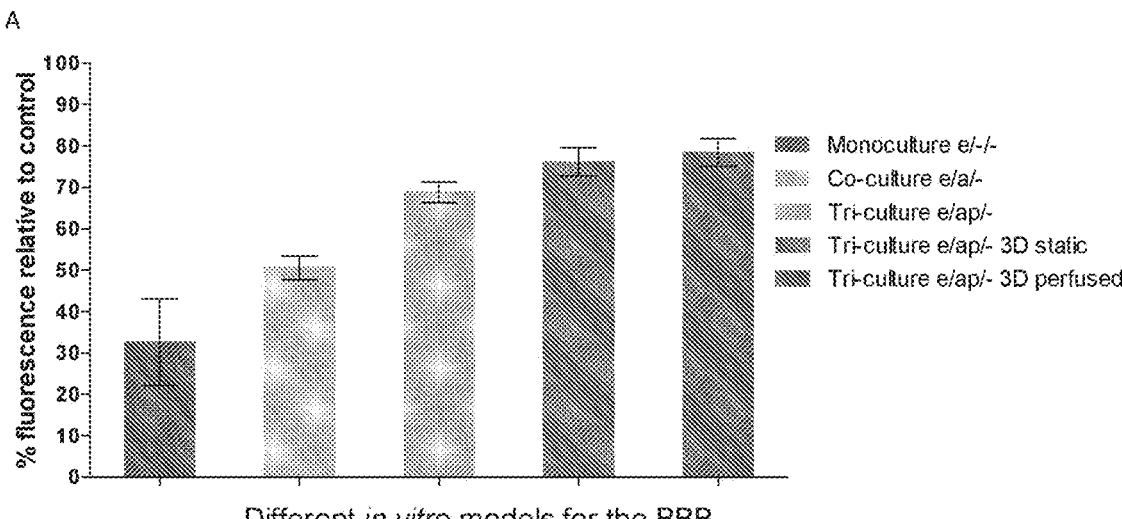
FIG. 7 illustrates the activity of efflux transporter proteins in different in vitro models: A. Activity of ABCB1 transporter (170 kDa). B. Activity of ABCG2 transporter (72 kDa). The graphs were plotted as percentage relative to the control which was defined as 0% activity of the efflux transporter at 4° C.
Figure 7:
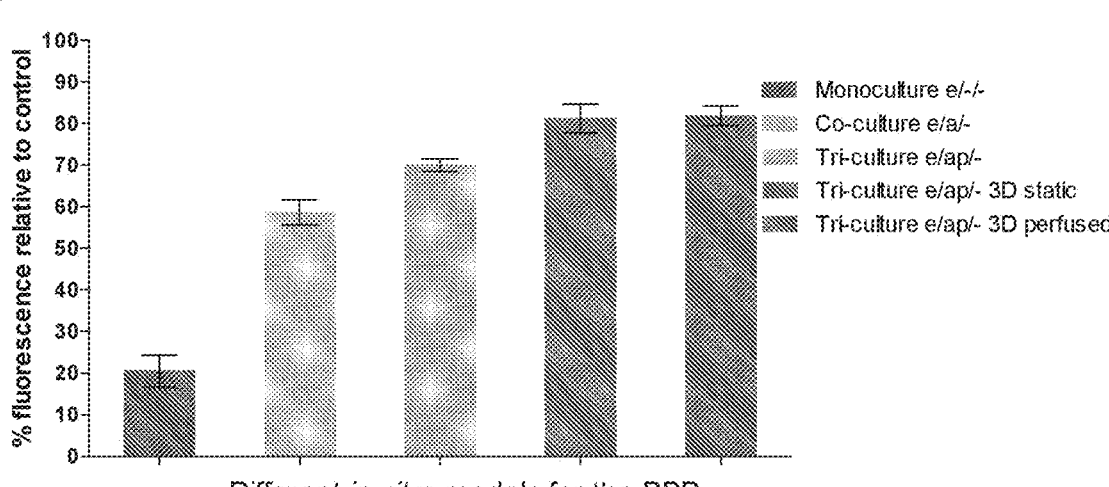

The functional activity of the efflux transporters was assessed by measuring the percentage of dye extruded by ABCB1 and ABCG2 transporters relative to a control (equivalent model at 4° C. normalised to 0% of dye efflux). As shown in FIGS. 7a and 7b, for ABCB1 and ABCG2 respectively, the highest activity was observed for the 3D model.

Figure 8:
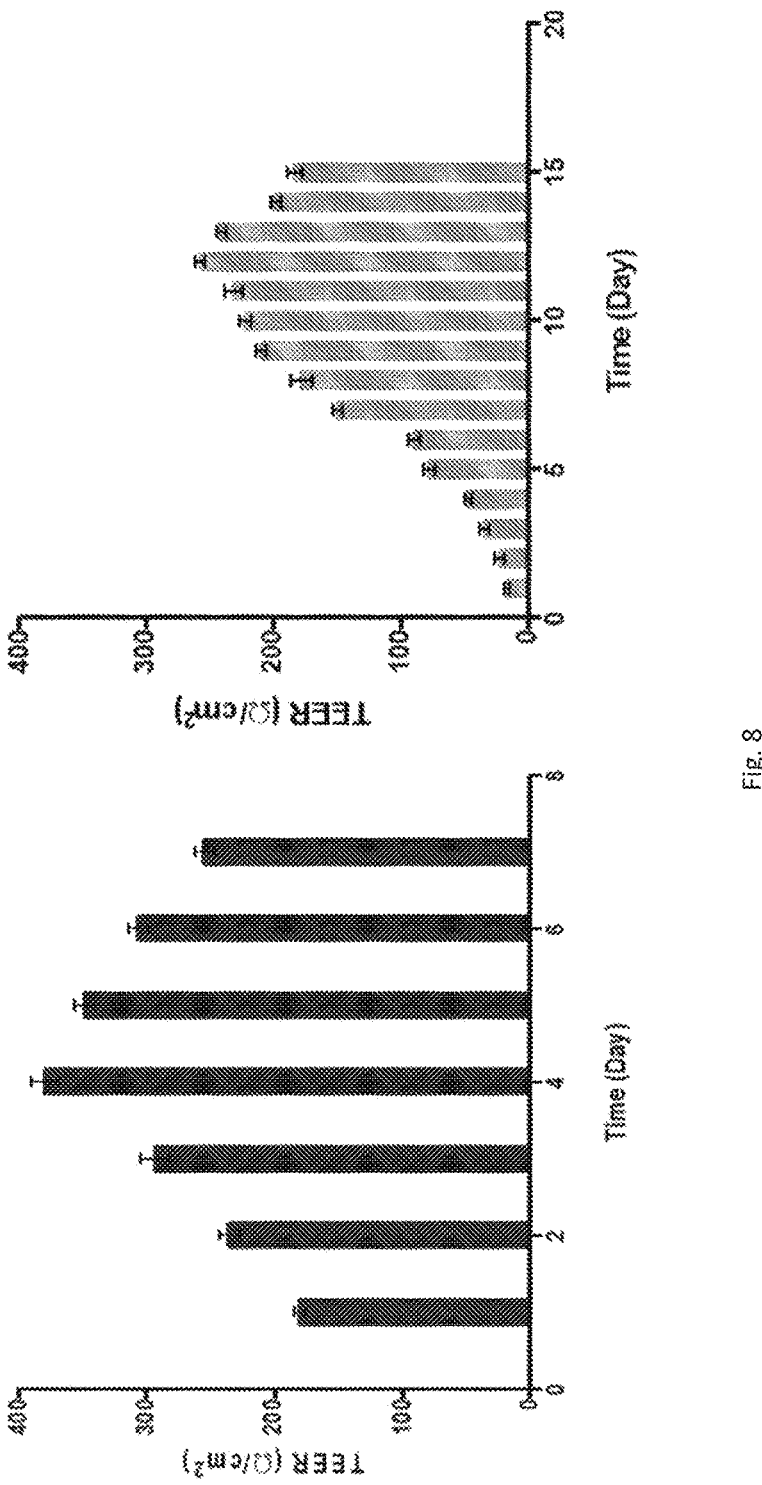
FIG. 8 illustrates TEER measurement comparisons of primary derived non-immortilised and immortalised cells in the tri-culture model: left) Tri-culture model set up using immortalised hcmec/d3 cells. right) Tri-culture model set up using primary derived hbmec cells.

2.4 Substitution of Primary Short-Term Endothelial Cells with Immortalised Endothelial Cells The most favourable composition of the in vitro blood brain barrier model would be use of short-term cultures of primary cells, however, to account for periods when availability of the HBMEC was scarce (not an issue with pericytes or astrocytes) we investigated the possibility of substitution of the HBMEC short term culture from primary cells with the immortalised hCMEC/D3. As seen in FIG. 8—right, the tri-culture model (e/ap/–) was substituted with immortalised HCMEC/D3 cell instead of primary hbmec cells (FIG. 8—left). The hCMEC/D3 cells shows a higher TEER value although earlier peak as compared to hCMEC/D3 cells and therefore would be a suitable alternative to HBMEC in the 3D model cultured under shear stress of the invention.

Figure 9:
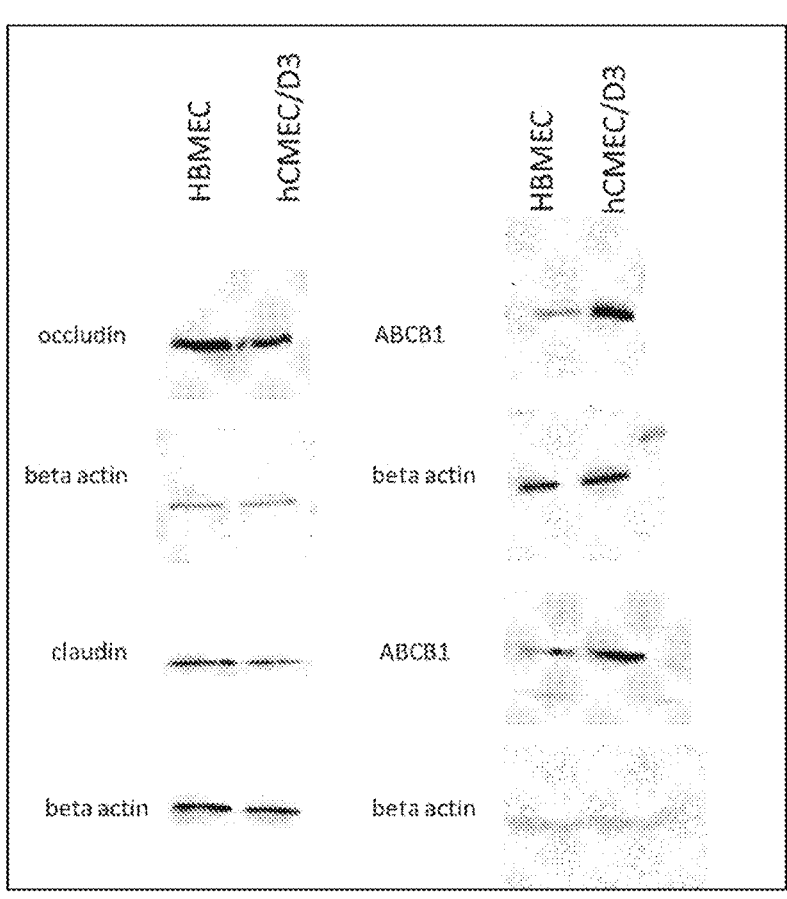
FIG. 9 Illustrates western blots of efflux transporters and tight-junction proteins in primary-derived (HBMEC) and immortilised (hCMEC/D3) endothelial cell lines for occludin (65 kDa); claudin-5 (23 kDa); ABCB1 (170 kDa) and ABCG2 (72 kDa). Each well was loaded with 10 μg protein and beta actin (42 kDa) was used as the loading control.

In addition, western immunoblotting to confirm expression of crucial proteins required for blood brain barrier model function (occludin, claudin-5, ABCB1, ABCG2) was conducted in the immortalised endothelial cells and found to be comparable to the primary short-term endothelial cells, confirming suitability of the hCM EC/D3 cells if the need for substitution of the primary cells arises (FIG. 9).

2.5 Measurement of Permeability Using FITC-Dextran

Figure 10:
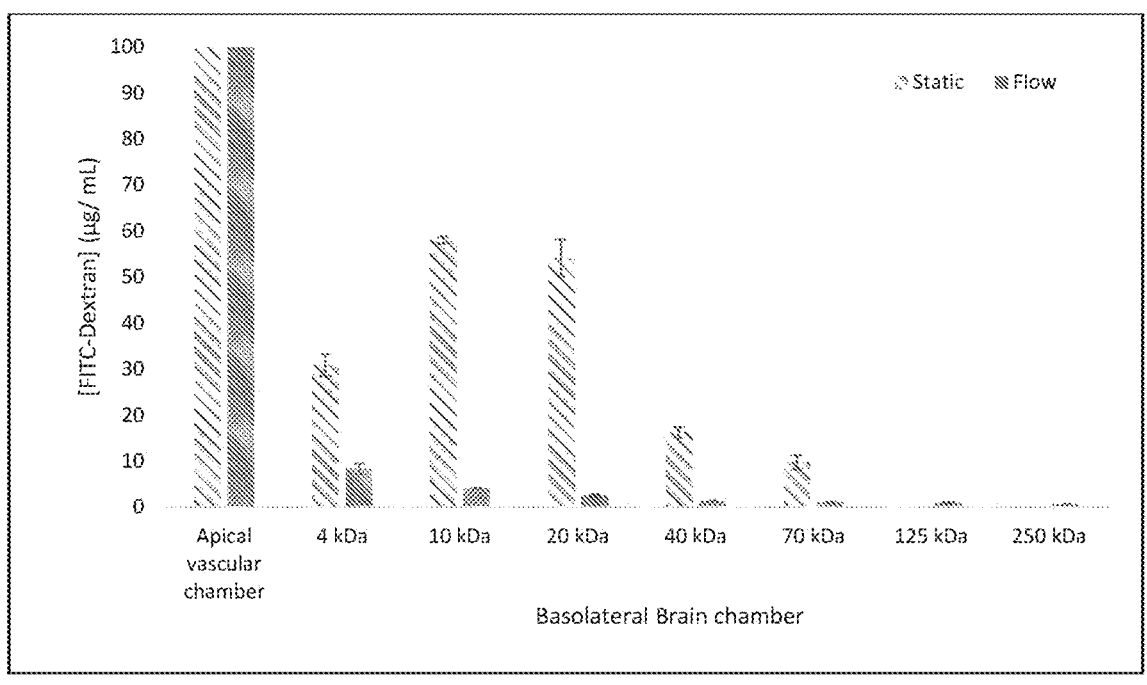
FIG. 10 Comparison of the concentration of FITC-dextran measured in the basolateral compartment of the blood brain barrier model following 60 minute incubation with 100 μg/mL of various molecular weight FITC dextrans delivered to the apical compartment of the blood brain barrier model cultured under static conditions verses shear stress conditions.

The blood brain barrier model was incubated for 60 minutes with 100 μg/mL of various molecular weight FITC-dextrans placed in the apical compartment of the model and cultured under static conditions verses shear stress flow conditions. FIG. 10 illustrates the marked increase in barrier model function when including shear stress flow compared to the static model as demonstrated by significantly greater exclusion of all molecular weight dextrans from moving into the basolateral brain compartment. The apparent permeability (Papp) of low molecular weight dextrans <4 kDa are used as a marker of low molecular weight solute and ion paracellular transport and the high molecular weight dextrans >40 kDa are a marker of proteins (11.2-14.6 nm) which should be excluded by the BBB. The Papp values decrease with increasing molecular weight compounds showing selective permeability. Also, the blood brain barrier model under shear stress in accordance with the invention more accurately reflects the in vivo function of the barrier as shown by a Papp=$0.47 \times 10^{-5}$ cm/s for 70 kDa FITC-dextran.

2.6 Applications of Blood Brain Barrier Model

Figure 11:
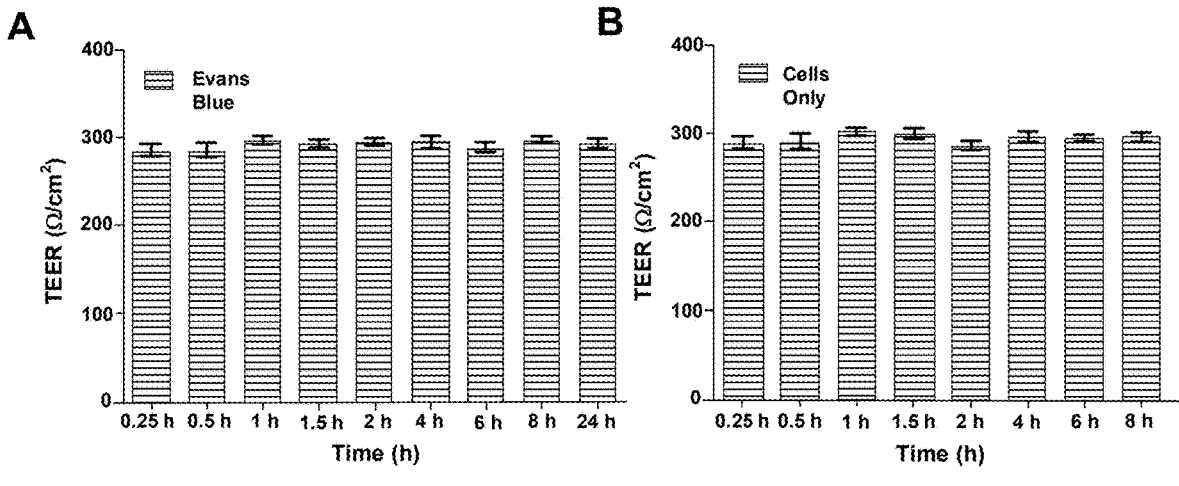
FIG. 11 Illustrates the change in transendothelial electrical resistance across the blood brain barrier model (A-D) and appearance of compound in the basolateral compartment (C and D secondary axis); A: no permeability across blood brain barrier model for known compound Evan's blue; B. no change in permeability of the control blood brain barrier model (no test compound) for the same experiment period; C. permeation of a test aptamer, designated GL21, which target glioma cells, is indicated by a decrease in TEER relative to the control blood brain barrier model and appearance in the basolateral compartment; and D. no permeation of a scrambled aptamer across the blood brain barrier model.
Figure 11:
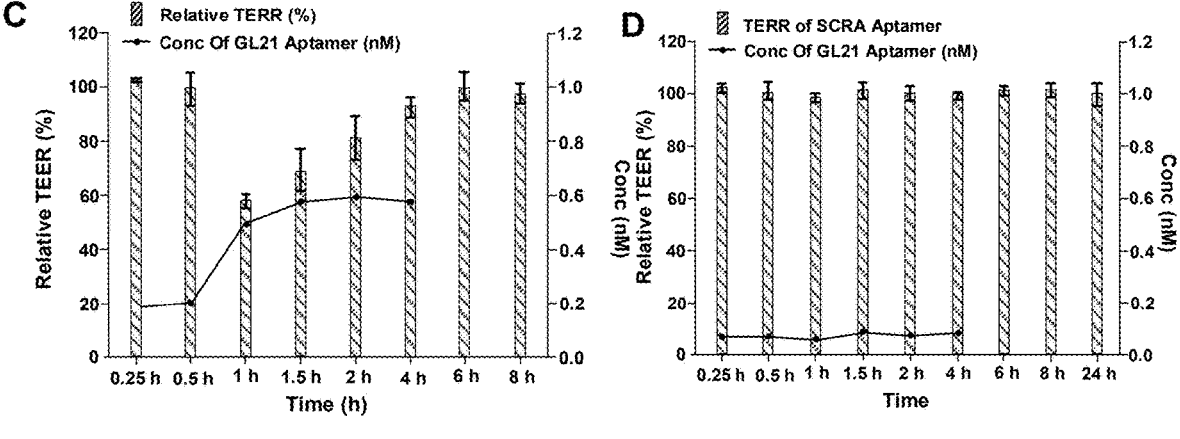

One example of an application of the blood brain barrier model of the invention is shown in FIG. 11. The blood brain barrier model was exposed to a test compound and the permeability of the barrier to said test compound was measured and compared to the permeability of the blood brain barrier model to known compounds.

The test compound chosen was an aptamer designated GL21 which is designed to cross the blood brain barrier and target glioma cells. The known compounds used were in this case Evan's Blue (an impermeable dye) and SCRA (an aptamer with a scrambled oligonucleotide sequence having no normal ability to permeate the blood brain barrier). FIG. 11 shows that the test compound was an ideal candidate for glioma targeting via the blood brain barrier and works as expected in the model. The drop in TEER values relative to the control blood brain barrier model, where no drug was introduced, are indicative of tight-junction opening and blood brain barrier model permeation. This was further confirmed by detection and measurement of the fluorescent-tagged test compound in the basolateral compartment of the blood brain barrier model. This example shows that the model of the invention can be successfully used in laboratory research to test the ability of compounds to cross the blood brain barrier.

Figure 12:
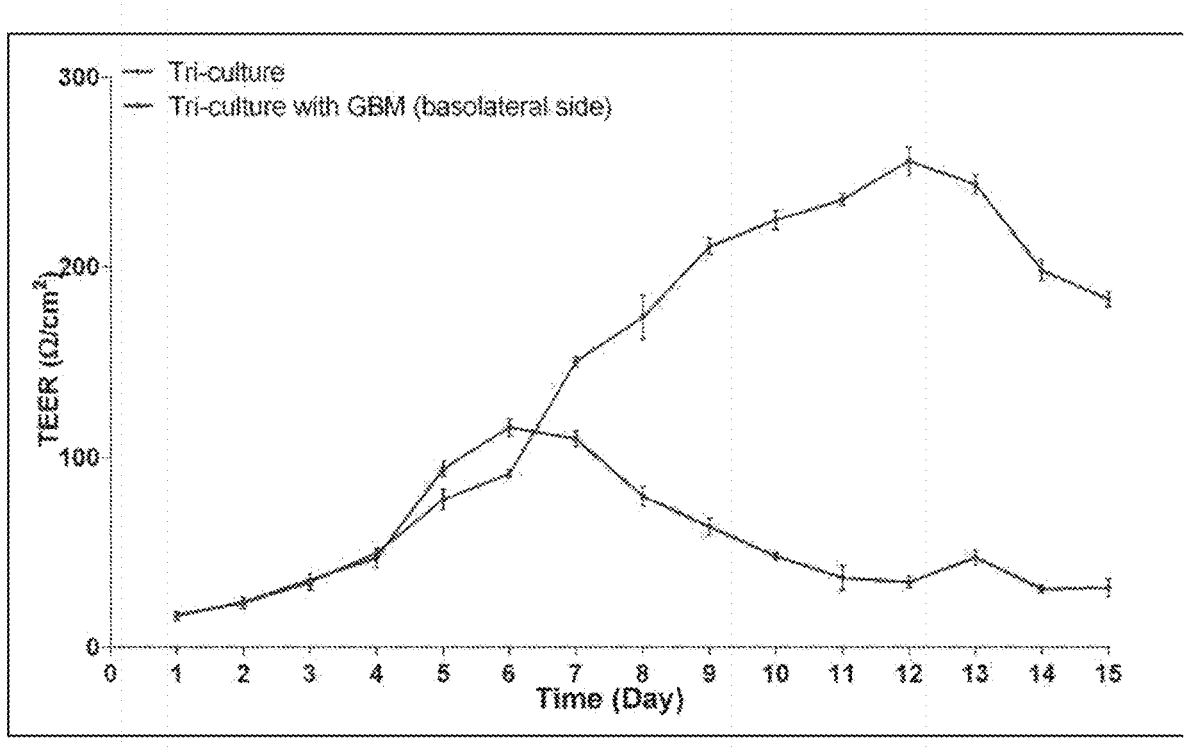
FIG. 12 Illustration of TEER values in the blood brain barrier model with glioma spheroids on the basolateral side compared to the healthy blood brain barrier model.

An example of a further application of the model of the invention is shown in FIG. 12. The influence of various disease states on the blood brain barrier can be observed and measured using the blood brain barrier model. FIG. 12 shows a blood brain barrier-glioma model. The influence of the glioma spheroids on the TEER across the blood brain barrier model was measured as described above. Glioma cells are highly invasive in nature, and as expected showed disruption to the intact barrier model. This is a phenomenon that has been documented in vivo and now can be shown in vitro using the blood brain barrier model of the invention.

Therefore the present model can be used to accurately reflect disease states for further in vitro research.

Figure 13:
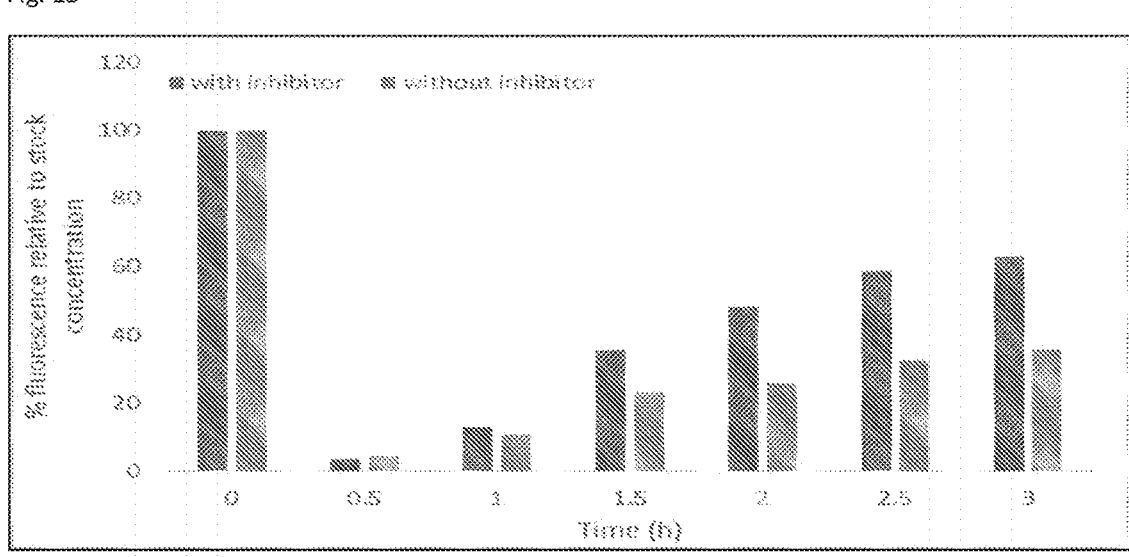
FIG. 13 Nanoparticle uptake by glioma spheroids on the blood brain barrier model (basolateral side); A. 0.33 μg/ml docetaxel loaded lipid nanoparticle tagged to rhodamine123; B. 0.33 μg/ml docetaxel loaded lipid nanoparticle tagged to rhodamine123 with transferrin ligand; C. 2.87 μg/ml curcumin loaded lipid nanoparticle. Stock concentration was the concentration of nanoparticles seeded on the apical side of the blood brain barrier model at time 0 h.
Figure 13:
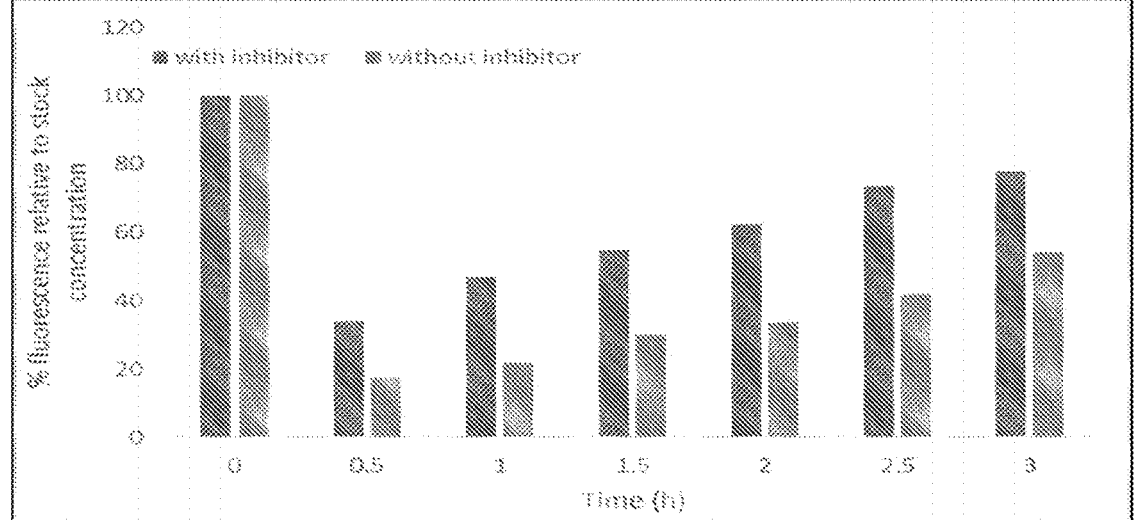
Figure 13:
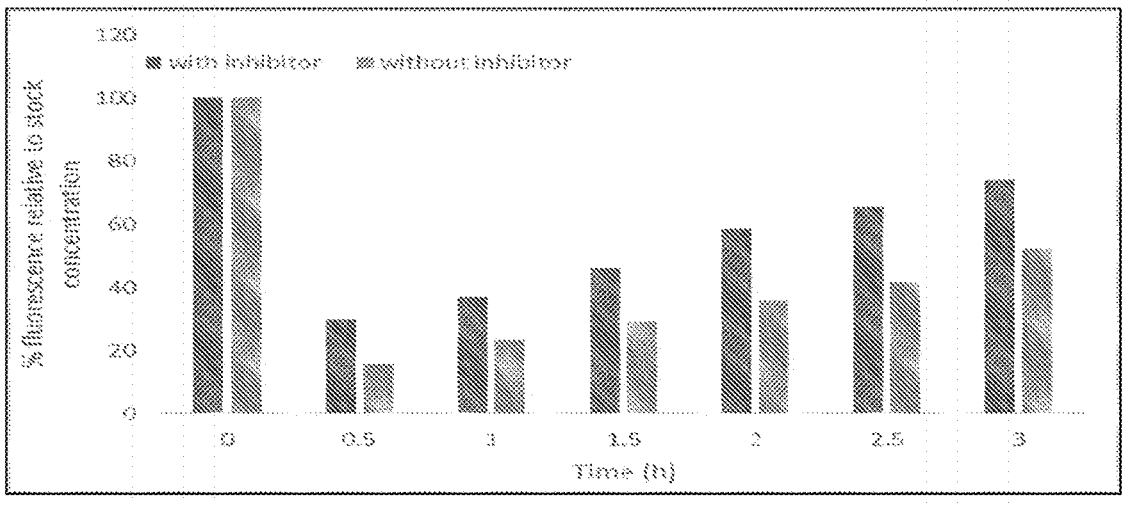

The blood brain barrier glioma model was further tested to determine the uptake of rhodamine123 tagged docetaxel loaded nanoparticles by the glioma spheroids. To determine the role of the efflux transporters, nanoparticle uptake was done in the presence and absence of an efflux transporter inhibitor vinblastine. FIG. 13 shows the accumulation of fluorescence in the glioma spheroids at different time points which reflects the uptake of the therapeutic nanoparticles by glioma relative to the fluorescence of the therapeutic nanoparticles introduced to the blood apical compartment (stock). The data demonstrated that the therapeutic nanoparticle compounds did indeed cross the blood brain barrier and penetrate glioma, highlighting how the model of the invention may be used to determine permeability of a test molecule relevant for treatment of CNS pathologies such as brain tumours.

Figure 14:
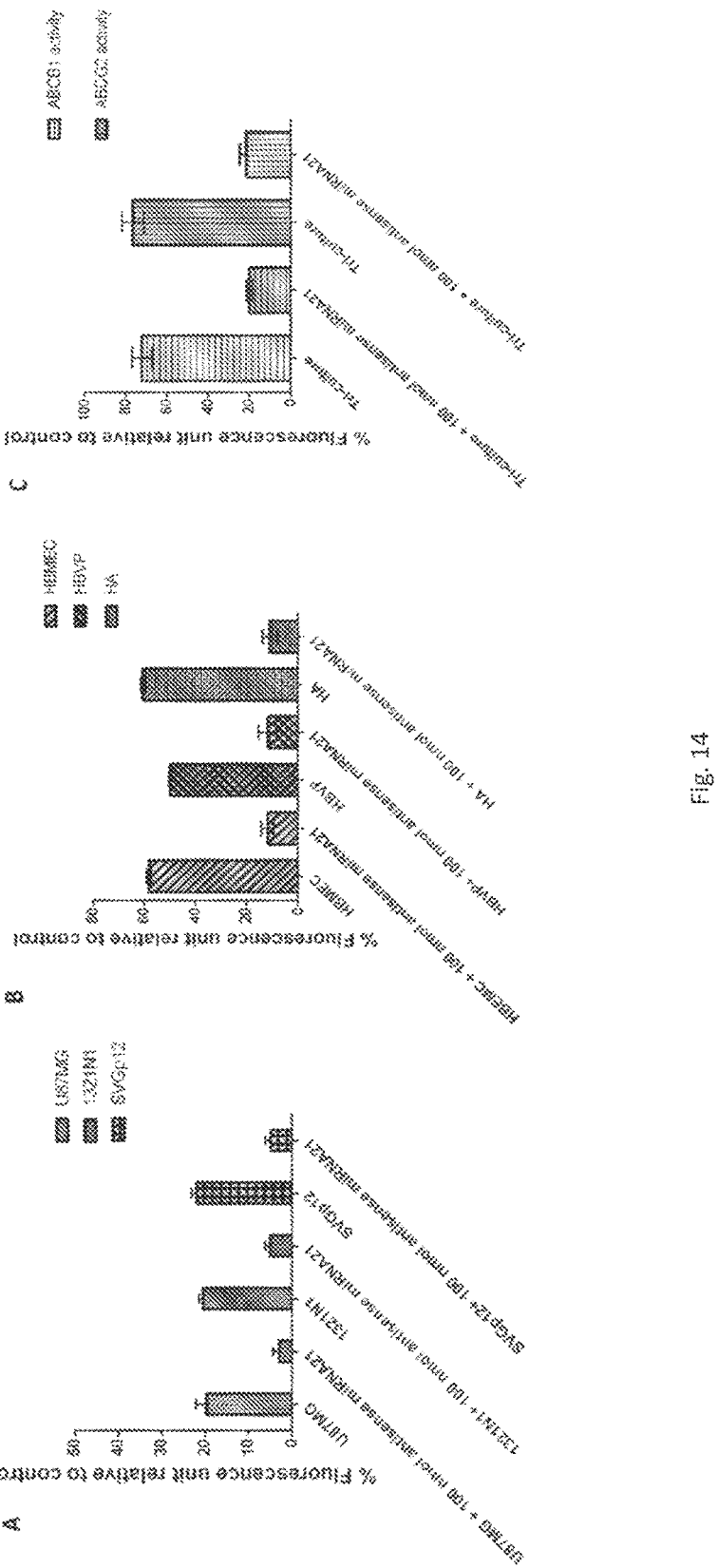
FIG. 14 Illustration of the effect of transfecting cells of a disease state blood brain barrier model comprising tumour cells on the activity of ABCB1 efflux: A: glioma cell lines; B: individual components of model and C: the full blood brain barrier model, each tested with antisense miRNA21. All the values were plotted as percentage relative to the control, which was 0% activity of the efflux transporter. The data points are means of three replicates from two experimental repeats and the error bars represent ±standard deviation (±SD) of six measurements from two experimental replicates.

Another example of how the blood brain barrier model of the invention can be used to investigate mediators of CNS disorders is shown in FIG. 14. This figure shows the effects of antisense miRNA21 on the barrier model properties. It was found that transfecting antisense miRNA21 into all cellular components of the blood brain barrier model reduced efflux activity of the ABCB1 transporter in individual cells and in the model as a whole. The results showed that activity of key drug transporter ABCB1 could be altered in the model, implying that the effects of other miRNA mediators purported to be involved in inflammation and disease progression can be studied. This result may have implications when elucidating the role of the blood brain barrier for CNS homeostasis in diseased and healthy states, since elevated expression of miRNA21 is associated with glioma progression.

Currently available in vitro blood brain barrier models have only been characterised for the physical attributes of the blood brain barrier, not the metabolic attributes of the blood brain barrier. Furthermore, there is an absence of multicellular models cultured using the relevant cell types of the neurovascular unit. Therefore there was an urgent need to develop a blood brain barrier model which is physiologically relevant and optimised for the metabolic characteristics of the barrier present at the blood and brain junctions.

The present inventors have solved this problem by producing a fully characterised, physiologically and metabolically relevant in vitro blood brain barrier model. The model provides a high TEER, maximum expression of tight junctions for the physical barrier, and high activity of drug metabolising enzymes and transporters for the metabolic barrier.

Applications of the model of the invention are numerous including: improving delivery of therapeutics to the CNS; elucidating new therapeutic targets at the blood brain barrier and furthering knowledge of the mechanism of disease in CNS pathologies. The establishment of this model takes account of all the essential components of the blood brain barrier and includes the essential properties an in vitro blood brain barrier model should have to accurately reflect the in vivo state.

The invention claimed is:

1. A structure comprising
   a cell population grown under a shear stress, comprising endothelial cells, astrocytes and pericytes wherein the cells are human primary derived non-immortalised cells;
   and a 3D (three dimensional) porous scaffold within which the cell population is organised, wherein the 3D porous scaffold is between about 150-250 µm thick, wherein the pores are about 25-80 µm in size, and wherein the scaffold comprises a porosity of over 90%;

wherein the structure has a TEER value of at least 450 $\Omega/cm^2$;

and wherein the structure comprises a ratio of endothelial cells:astrocytes:pericytes of about 7.5:1:1 to about 5:1:1.

2. A structure according to claim 1, wherein the cells are derived from the brain.

3. A structure according to claim 1, wherein the endothelial cells and astrocytes have a passage number of less than 10 and the pericytes have a passage number of less than 6.

4. A structure according to claim 1, wherein the scaffold is coated with a coating material.

5. A structure according to claim 4 wherein the coating material is a biopolymer selected from fibronectin, collagen, poly-1-lysine, or Perlecan.

6. A structure according to claim 4 wherein the coating material is present at a concentration of about 1-20 $\mu g/cm^2$ of the surface area of the scaffold.

7. A structure according to claim 1 wherein the TEER value is between about 450 $\Omega/cm^2$ and 1000 $\Omega/cm^2$.

8. A structure according to claim 7, wherein the TEER value is between about 700 $\Omega/cm^2$ and 800 $\Omega/cm^2$.

9. A blood brain barrier model comprising a container comprising the structure of claim 1;

wherein the structure separates a first chamber located on a first side of the structure and a second chamber located on a second side of the structure;

and wherein the first chamber contains a first liquid in contact with the first side of the structure, and the second chamber contains a second liquid in contact with the second side of the structure.

10. A method of making a structure according to claim 1, the method comprising the steps of:

(a) Distributing a cell population comprising endothelial cells, astrocytes and pericytes, wherein the cells are human primary derived non-immortalised cells, in a 3D (three dimensional) porous scaffold; and (b) Culturing the cell population under shear stress.

11. A method of investigating the permeability of the blood brain barrier, the method comprising:

(a) Exposing the blood brain barrier model of claim 9 to a test molecule; and (b) Measuring the permeability of the blood brain barrier model.

12. A structure according to claim 4, wherein the coating material comprises fibronectin and is present at a concentration of about 5 $\mu g/cm^2$ of the surface area of the scaffold.

* * * * *